(12) United States Patent
Stein et al.

(10) Patent No.: US 8,357,664 B2
(45) Date of Patent: *Jan. 22, 2013

(54) ANTISENSE ANTIVIRAL COMPOUND AND METHOD FOR TREATING INFLUENZA VIRAL INFECTION

(75) Inventors: David A. Stein, Corvallis, OR (US); Qing Ge, Santa Cruz, CA (US); Jianzhu Chen, Lexington, MA (US); Patrick L. Iversen, Corvallis, OR (US); Hong M. Moulton, Corvallis, OR (US)

(73) Assignees: AVI BioPharma, Inc., Corvallis, OR (US); M.I.T., Cambridge, MA (US)

( * ) Notice: Subject to any disclaimer, the term of this patent is extended or adjusted under 35 U.S.C. 154(b) by 615 days.

This patent is subject to a terminal disclaimer.

(21) Appl. No.: 11/259,434

(22) Filed: Oct. 25, 2005

(65) Prior Publication Data
US 2006/0148747 A1 Jul. 6, 2006

Related U.S. Application Data

(60) Provisional application No. 60/622,077, filed on Oct. 26, 2004.

(51) Int. Cl.
*A61K 48/00* (2006.01)
(52) U.S. Cl. ...... 514/44; 536/24.5; 536/24.31; 536/24.1
(58) Field of Classification Search ............ None
See application file for complete search history.

(56) References Cited

U.S. PATENT DOCUMENTS

| | | | |
|---|---|---|---|
| 5,142,047 A | 8/1992 | Summerton et al. | |
| 5,185,444 A | 2/1993 | Summerton et al. | |
| 5,194,428 A * | 3/1993 | Agrawal et al. | 514/44 |
| 5,495,006 A | 2/1996 | Climie et al. | |
| 5,576,302 A | 11/1996 | Cook et al. | |
| 5,580,767 A | 12/1996 | Cowsert et al. | |
| 5,637,573 A | 6/1997 | Agrawal et al. | 514/44 |
| 5,698,685 A | 12/1997 | Summerton et al. | |
| 5,702,891 A | 12/1997 | Kolberg et al. | |
| 5,734,039 A | 3/1998 | Calabretta et al. | |
| 5,738,985 A | 4/1998 | Miles et al. | |
| 5,801,154 A | 9/1998 | Baracchini et al. | |
| 5,892,023 A | 4/1999 | Pirotzky et al. | |
| 5,955,318 A | 9/1999 | Simons et al. | |
| 5,989,904 A | 11/1999 | Das et al. | |
| 6,060,456 A | 5/2000 | Arnold, Jr. et al. | |
| 6,133,246 A | 10/2000 | McKay et al. | |
| 6,174,868 B1 | 1/2001 | Anderson et al. | |
| 6,214,555 B1 | 4/2001 | Leushner et al. | |
| 6,228,579 B1 | 5/2001 | Zyskind et al. | |
| 6,239,265 B1 | 5/2001 | Cook | |
| 6,258,570 B1 | 7/2001 | Glustein et al. | |
| 6,306,993 B1 | 10/2001 | Rothbard et al. | |
| 6,365,351 B1 | 4/2002 | Iversen | |
| 6,365,577 B1 | 4/2002 | Iversen | |
| 6,391,542 B1 | 5/2002 | Anderson et al. | |
| 6,495,663 B1 | 12/2002 | Rothbard et al. | |
| 6,669,951 B2 | 12/2003 | Rothbard et al. | |
| 6,677,153 B2 | 1/2004 | Iversen | |
| 6,784,291 B2 | 8/2004 | Iversen et al. | |
| 6,828,105 B2 | 12/2004 | Stein et al. | |
| 6,841,542 B2 | 1/2005 | Bartelmez et al. | |
| 6,881,825 B1 | 4/2005 | Robbins et al. | |
| 7,049,431 B2 | 5/2006 | Iversen et al. | |
| 7,094,765 B1 | 8/2006 | Iversen et al. | |
| 7,115,374 B2 | 10/2006 | Linnen et al. | |
| 7,507,196 B2 | 3/2009 | Stein et al. | |
| 2003/0087851 A1 | 5/2003 | Takaku et al. | 514/44 |
| 2003/0166588 A1 | 9/2003 | Iversen et al. | |
| 2003/0171311 A1 | 9/2003 | Blatt et al. | |
| 2003/0171335 A1 * | 9/2003 | Stein et al. | 514/81 |
| 2003/0224353 A1 | 12/2003 | Stein et al. | |
| 2004/0072239 A1 | 4/2004 | Renaud et al. | |
| 2004/0110296 A1 | 6/2004 | Vargeese et al. | |
| 2004/0259108 A1 | 12/2004 | Linnen et al. | |
| 2004/0265879 A1 | 12/2004 | Iversen et al. | |

(Continued)

FOREIGN PATENT DOCUMENTS

JP 9-121867 A 5/1997

(Continued)

OTHER PUBLICATIONS

Rothbard et al. Arginine rich molecular transporters for drug delivery: role of backbone spacing in cellular uptake. J. Med. Chem. 2002, vol. 45: 3612-3618.*
Scanlon, Ki. Anti-Genes: siRNA, Riboyzmes and Antisense. Current Pharmaceutical Biotechnology, 2004, vol. 5L 415-420.*
Green et al. Antisense oligonucleotides: an evolving technology for the modulation of gene expression in human disease. J Am Coll Surg (2000), vol. 191: 93-105. Elsevier.*
Jen et al. Suppresion of Gene Expression by Targeted Disruption of Messenger RNA: Available Options and Current Strategies. Stem Cells (2000), vol. 18:307-319. AlphaMed Press.*
Crooke, S. Antisense Research and Application, Chapter 1, Springer-Verlag, New York. 1998.*
Abe et al. Nucleosides and Nucleotides 1998, vol. 17:471-478.*
Winter 1982, vol. 10: 2135-2143.*
Agrawal et al., *Molecular Med. Today*, 6:72-81 (2000).
Agrawal, S., S. H. Mayrand, et al. (1990). "Site-specific excision from RNA by RNase H and mixed-phosphate-backbone oligodeoxynucleotides." *Proc Natl Acad Sci U S A* 87(4): 1401-5.

(Continued)

*Primary Examiner* — Kimberly Chong
(74) *Attorney, Agent, or Firm* — Seed IP Law Group PLLC

(57) ABSTRACT

The invention provides antisense antiviral compounds and methods of their use and production in inhibition of growth of viruses of the Orthomyxoviridae family and in the treatment of a viral infection. The compounds are particularly useful in the treatment of influenza virus infection in a mammal. The antisense antiviral compounds are substantially uncharged morpholino oligonucleotides having 1) a nuclease resistant backbone, 2) 12-40 nucleotide bases, and 3) a targeting sequence of at least 12 bases in length that hybridizes to a target region selected from the following: a) the 5' or 3' terminal 25 bases of the negative sense viral RNA segment of Influenzavirus A, Influenzavirus B and Influenzavirus C; b) the terminal 25 bases of the 3' terminus of the positive sense cRNA and; and c) the 50 bases surrounding the AUG start codon of an influenza viral mRNA.

7 Claims, 9 Drawing Sheets

U.S. PATENT DOCUMENTS

| | | | |
|---|---|---|---|
| 2005/0176661 | A1 | 8/2005 | Vaillant et al. |
| 2006/0063150 | A1 | 3/2006 | Iversen et al. |
| 2006/0149046 | A1 | 7/2006 | Arar |
| 2006/0269911 | A1 | 11/2006 | Iversen et al. |
| 2007/0066556 | A1 | 3/2007 | Stein et al. |
| 2007/0129323 | A1 | 6/2007 | Stein et al. |
| 2007/0265214 | A1 | 11/2007 | Stein et al. |

FOREIGN PATENT DOCUMENTS

| | | |
|---|---|---|
| JP | 11-137260 A | 5/1999 |
| WO | WO 98/12312 A1 | 3/1998 |
| WO | WO 02/26968 A1 | 4/2002 |
| WO | WO 02/068637 A2 | 9/2002 |
| WO | WO 03/033657 A2 | 4/2003 |
| WO | WO 2005/007805 A1 | 1/2005 |
| WO | WO 2005/013905 A1 | 2/2005 |
| WO | WO 2005/030800 A1 | 4/2005 |
| WO | WO 2006/047683 A2 | 4/2006 |

OTHER PUBLICATIONS

Banerjee, R. and A. Dasgupta (2001). "Interaction of picornavirus 2C polypeptide with the viral negative-strand RNA." *J Gen Virol* 82(Pt 11): 2621-7.

Banerjee, R. and A. Dasgupta (2001). "Specific interaction of hepatitis C virus protease/helicase NS3 with the 3'-terminal sequences of viral positive- and negative-strand RNA." *J Virol* 75(4): 1708-21.

Banerjee, R., A. Echeverri, et al. (1997). "Poliovirus-encoded 2C polypeptide specifically binds to the 3'-terminal sequences of viral negative-strand RNA." *J Virol* 71(12): 9570-8.

Banerjee, R., W. Tsai, et al. (2001). "Interaction of poliovirus-encoded 2C/2BC polypeptides with the 3' terminus negative-strand cloverleaf requires an intact stem-loop b." *Virology* 280(1): 41-51.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Branch et al., *Trends in Biochem. Sci.*, 23:45-50 (1998).

Chirilla et al., *Biomaterials*, 23:321-342 (2002).

Cox, N. J. and K. Subbarao (1999). "Influenza." *Lancet* 354(9186): 1277-82.

Cox, N. J. and K. Subbarao (2000). "Global epidemiology of influenza: past and present." *Annu Rev Med* 51: 407-21.

Crooke, S.T., *Antisense Res. and Applica.*, 1-50. S. Crooke, ed. Springer. (1999).

Cross, C. W., J. S. Rice, et al. (1997). "Solution structure of an RNA x DNA hybrid duplex containing a 3'-thioformacetal linker and an RNA A-tract." *Biochemistry* 36(14): 4096-107.

Dagle, J. M., J. L. Littig, et al. (2000). "Targeted elimination of zygotic messages in *Xenopus laevis* embryos by modified oligonucleotides possessing terminal cationic linkages." *Nucleic Acids Res* 28(10): 2153-7.

Ding, D., S. M. Grayaznov, et al. (1996). "An oligodeoxyribonucleotide N3'→ P5' phosphoramidate duplex forms an A-type helix in solution." *Nucleic Acids Res* 24(2): 354-60.

Egholm, M., O. Buchardt, et al. (1993). "PNA hybridizes to complementary oligonucleotides obeying the Watson-Crick hydrogen-bonding rules." *Nature* 365(6446): 566-8.

Feigner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Gilbert et al., *J. Clinical Epidemiology*, 54:68-85 (2001).

Holland, J. (1993). *Emerging Virus*. S. S. Morse. New York and Oxford, Oxford University Press: 203-218.

Hudziak et al., *Antisnese &Nucleic Acid Drug Dev.*, 6:267-272 (1996).

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Markoff, L. (2003). "5'- and 3'-noncoding regions in flavivirus RNA." *Adv Virus Res* 59: 177-228.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.

Moulton, H. M., M. H. Nelson, et al. (2004). "Cellular uptake of antisense morpholino oligomers conjugated to arginine-rich peptides." *Bioconjug Chem* 15(2): 290-9.

Nelson, M. H., D. A. Stein, et al. (2005). "Arginine-rich peptide conjugation to morpholino oligomers: effects on antisense activity and specificity." *Bioconjug Chem* 16(4): 959-66.

Neuman, B. W., D. A. Stein, et al. (2004). "Antisense Morpholino-Oligomers Directed against the 5' End of the Genome Inhibit Coronavirus Proliferation and Growth{dagger}." *J. Virol.* 78(11): 5891-5899.

O'Ryan, M. (1992). *Clinical Virology Manual*. S. Spector and G. Lancz. New York, Elsevier Science: 361-396.

Palu et al., *J. Biotech.*, 68:1-13 (1999).

Pardigon, N. and J. H. Strauss (1992). "Cellular proteins bind to the 3' end of Sindbis virus minus-strand RNA." *J Virol* 66(2): 1007-15.

Pardigon, N., E. Lenches, et al. (1993). "Multiple binding sites for cellular proteins in the 3' end of Sindbis alphavirus minus-sense RNA." *J Virol* 67(8): 5003-11.

Paul, A. V. (2002). Possible unifying mechanism of picornavirus genome replication. *Molecular Biology of Picornaviruses*. B. L. Semler and E. Wimmer. Washington, DC, ASM Press: 227-246.

Roehl, H. H. and B. L. Semler (1995). "Poliovirus infection enhances the formation of two ribonucleoprotein complexes at the 3' end of viral negative-strand RNA." *J Virol* 69(5): 2954-61.

Roehl, H. H., T. B. Parsley, et al. (1997). "Processing of a cellular polypeptide by 3CD proteinase is required for poliovirus ribonucleoprotein complex formation." *J Virol* 71(1): 578-85.

Smith, A. W., D. E. Skilling, et al. (1998). "Calicivirus emergence from ocean reservoirs: zoonotic and interspecies movements." *Emerg Infect Dis* 4(1): 13-20.

Summerton et al., *Biochim et. Biophys. Acta*, 1489:141-158 (1999).

Summerton, J. and D. Weller (1997). "Morpholino antisense oligomers: design, preparation, and properties." *Antisense Nucleic Acid Drug Dev* 7(3): 187-95.

Summerton et al., *Antisense & Nucleic Acid Drug Development*, 7:63-70 (1997).

Toulme, J. J., R. L. Tinevez, et al. (1996). "Targeting RNA structures by antisense oligonucleotides." *Biochimie* 78(7): 663-73.

Williams, A. S., J. P. Camilleri, et al. (1996). "A single intra-articular injection of liposomally conjugated methotrexate suppresses joint inflammation in rat antigen-induced arthritis." *Br J Rheumatol* 35(8): 719-24.

Wu, G. Y. and C. H. Wu (1987). "Receptor-mediated in vitro gene transformation by a soluble DNA carrier system." *J Biol Chem* 262(10): 4429-32.

Xu, W. Y. (1991). "Viral haemorrhagic disease of rabbits in the People's Republic of China: epidemiology and virus characterisation." *Rev Sci Tech* 10(2): 393-408.

Zollinger et al., *Transactions of Royal Soc of Tropical Medicine and Hygiene.*, 85(Supp. 1) pp. 37-43 (1991).

Zuker, M. (2003). "Mfold web server for nucleic acid folding and hybridization prediction." *Nucleic Acids Res* 31(13): 3406-15.

Agrawal et al. "Oligodeoxynucleoside phosphoramidates and phosphorothioates as inhibitors of human immunodeficiency virus", *Proc Natl Acad Sci U S A.*, 85(19):7079-7083 (1988).

Bailey, C. P., J. M. Dagle et al., "Cationic oligonucleotides can mediate specific inhibition of gene expression in *Xenopus oocytes.*" *Nucleic Acids Res*, 26(21): 4860-7 (1998).

Barawkar, D. A. and T. C. Bruice, "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A*, 95(19): 11047-52. (1998).

Basler et al., "The Ebola virus VP35 protein functions as a type I IFN antagonist", *Proc. Natl. Acad. Sci. U.S.A.*, 97(22):12289-12294 (2000).

Brasey et al., "The leader of human immunodeficiency virus type 1 genomic RNA harbors an internal ribosome entry segment that is active during the G2/M phase of the cell cycle", *Journal of Virology*, 77(7):3939-3949 (2003).

Clarke et al., "Organization and expression of calicivirus genes", *J. Infect. Diseases*, 181:S309-S316 (2000).

The International Search Report and Written Opinion for PCT/US2007/011435, search report dated, Sep. 29, 2008, 10 pages (2008).

Corey et al., Morpgolino Antisnese Oligonucleotides: Tools for Investigating Vertebrate Development, Genome Biology, 2(5):1015.1-1015.3 (2001).

Deas, T.S., et al., "Inhibition of flavivirus infections by antisense oligomers specifically suppressing viral translation and RNA replication", *Journal of Virology*, 79(8):4599-4609, (2005).

Freier, S.M., in Antisense Drug Technology: Principles, Strategies, and Applications, Chapter 5, pp. 107-118 (2001).

Genbank Accession No. AF304460, Human coronavirus 229E, complete genome (Jul. 2001).

Hanacek et al., "Antisense oligonucleotide inhibition of hepatitis C virus gene expression in transformed hepatocytes", *Journal of Virology*, 70:5203-5212 (1996).

Jaeger, J.A. et al., "Improved predictions of secondary structures for RNA", *Proc. Natl. Acad. Sci. USA*, 86:7706-7710 (1989).

Johannes et al., "Identification of eukaryotic mRNAs that are translated at reduced cap binding complex eIF4F concentrations using a cDNA microarray", *Proc. Natl. Acad. Sci. USA*, 96(23):13118-13123 (1999).

Jubin, R., et al., "Hepatitis C virus internal ribosome entry site (IRES) stem loop IIId contains a phylogenetically conserved GGG triplet essential for translation and IRES folding", *Journal of Virology*, 74(22):10430-10437 (2000).

Linkletter, B. A. and Bruice, T.C., "Solid-phase synthesis of positively charged deoxynucleic guanidine (DNG) modified oligonucleotides containing neutral urea linkages: Effect of charge deletions on binding and fidelity." *Bioorg. Med. Chem.* 8(11): 1893-1901 (2000).

Liu et al., "Structural and functional analysis of the 5' untranslated region of coxsackievirus B3 RNA: In vivo translational and infectivity studies of full-length mutants", *Virology*, 265:206-217 (1999).

Lopez De Quinto S. et al., "Involvement of the aphthovirus RNA region located between the two functional AUGs in start codon selection", *Virology*, 255(2):324-336 (1999).

McCaffey et al., "A potent and specific morpholino antisense inhibitor of hepatitis C translation in mice", *Hepatology*, 38(2):503-508 (2003).

Micklefield, J., "Backbone modification of nucleic acids: synthesis, structure and therapeutic applications." *Curr Med Chem*, 8(10):1157-79 (2001).

Moulton et al., Abstracts of Papers American Chemical Society National Meeting 226 (1-2): Biol 75 (Sep. 7-11, 2003).

National Center for Biotechnology Information Report No. AF029248 from NCBI Genome Database (2000).

National Center for Biotechnology Information Report No. NC_002645 from NCBI Genome Database (2001).

National Center for Biotechnology Information Report No. AY274119 from NCBI Genome Database (2003).

Orr et al., *Current Opinion in Molecular Therapeuctics, Current Drugs*, 2(3):325-331 (2000).

Partridge et al., "A simple method for delivering morpholino antisense oligos into the cytoplasm of cells", *Antisense Nucleic Acid Drug Dev.*, 6(3):169-75 (1996).

Peter M. Fischer, "Cellular uptake mechanisms and potential therapeutic utility of peptidic cell delivery vectors: progress 2001-2006" Published online 2006 in Wiley Interscience, www.interscience.wiley.com pp. 1-41 (2006).

Raviprakash, K., et al., "Inhibition of dengue virus by novel, modified antisense oligonucleotides", *Journal of Virology*, 69(1):69-74, (1995).

Sankar e al., "Antisense oligonucleotide inhibition of encephalomyocarditis virus RNA translation", *European Journal of Biochemistry*, 184(1):39-45 (1989).

Shengqi et al., "Synthesis of Antisense Phosphothioate Oligodeoxynucleotides of Dengue Fever Virus and Their Anti-Viral Activity", *Progress in Biochemistry and Biophsics*, 24:64-68 (English Translation) (1997).

Siprashvilli et al., "Gene transfer via reversible plasmid condensation with cysteine-flanked, internally spaced arginine-rich peptides", *Human Gene Therapy*, 14:1225-1233 (2003).

Smith et al., "Antisense treatment of caliciviridae: an emerging disease agent of animals and humans", *Current Opinion Molecular Therapeutcis*, 4(2):177-184 (2002).

Smith, R.M. and Wu, G.Y., "Secondary structure and hybridization accessibility of the hepatitis C virus negative strand RNA 5'-terminus", *Journal of Viral Hepatitis*, 11:115-123 (2004).

Stein et al., "A specificity comparison of four antisense types: morpholino, 2'-O-methyl RNA, DNA, and phosphorothioate DNA", *Antisense & Nucleic Acid Drug Development*, 7(3):151-7 (1997).

Stein et al., "Inhibition of Vesivirus infections in mammalian tissue culture with antisense morpholino oligomers", *Antisense & Nucleic Acid Drug Development*, 11(5):317-325 (2001).

Taylor et al., "Antisense oligonucleotides: a systematic high-throughput approach to target validation and gene function determination", *Drug Discovery Today*, 4:562-567 (1999).

Thiel et al., "Infectious RNA transcribed in vitro from a cDNA copy of the human coronavirus genome cloned in vaccinia virus", *Journal of General Virology*, 82:1273-1281 (2001).

Wages et al., "Affinity purification of RNA: sequence-specific capture by nonionic morpholino probes", *Biotechniques*, 23:1116-1121 (1997).

Wang et al., "Specific inhibition of coxsackievirus B3 translation and replication by phosphorothioate antisense oligodeoxynucleotides", *Antimicrobial Agents Chemotherapy*, 45(4):1043-1052 (2001).

Wei et al., "Human immunodeficiency virus type-1 reverse transcription can be inhibited in vitro by oligonucleotides that target both natural and synthetic tRNA primers", *Nucleic Acids Res.*, 28:3065-3074 (2000).

Wilson et al., "Naturally occurring dicistronic cricket paralysis virus RNA is regulated by two internal ribosome entry sites", *Mol. Cell. Biol.*, 20(14):4990-4999 (2000).

Wu et al., "Specific inhibition of hepatitis B viral gene expression in vitro by targeted antisense oligonucleotides", *J. Biol. Chem.*, 267:12436-12439 (1992).

Yuan et al., "A phosphorothioate antisense oligodeoxynucleotide specifically inhibits coxsackievirus B3 replication in cardiomyocytes and mouse hearts", *Labotratory Investigation*, 84:703-714 (2004).

Zhang et al., "Antisense oligonucleotide inhibition of hepatitis C virus (HCV) gene expression in livers of mice infected with an HCV-vaccinia virus recombinant", *Antimicrobial Agents Chemotherapy*, 43(2):347-353 (1999).

Arora and Iversen, "Redirection of drug metabolism using antisense technology", *Curr. Opin Mol. Ther.*, 3(3):249-257 (2001).

Borio, L. et al., "Hemorrhagic fever viruses as biological weapons: medical and public health management", *The Journal of the American Medical Association*, 287(18):2391-2405 (2002).

Bray, M. et al., "A mouse model for evaluation of prophylaxis and therapy of Ebola hemorrhagic fever", *The Journal of Infectious Diseases*, 178(3):651-661 (1998).

Burnett, J.C. et al., "The evolving field of biodefence: therapeutic developments and diagnostics", *Natural Review Drug Discovery*, 4:281-297 (2005).

The European Search Report for European application 05796604.6, search report dated, Jan. 5, 2009, 8 pages (2009).

Connolly, B.M. et al., "Pathogenesis of experimental Ebola virus infection in guinea pigs", *The Journal of Infectious Diseases*, 179(Suppl. 1):S203-S217 (1999).

Feldmann, H. et al., "Ebola Virus: from Discovery to Vaccine", *Nature Review Immunology*, 3(8):677-685 (2003).

Feldman, H. et al., *Current Topics in Microbiology and Immunology*, Classsification, Structure, and Replication of Filoviruses, pp. 1-21 (1999).

Feldman, H. et al., "Molecular Biology and Evolution of Filoviruses", *Arch. Virol.*, 7(Suppl.):81-100 (1993).

Geisbert, T.W. and Hensley, L.E.,"Ebola virus: new insights into disease aetiopathology and possible therapeutic interventions", *Expert Reviews in Molecular Medicine*, 6(20):1-24 (2004).

Geisbert, T.W. et al.,"Treatment of Ebola virus infection with a recombinant inhibitor of factor VIIa/tissue factor: a study in rhesus monkeys", *The Lancet*, 362(9400):1953-1958 (2003).

Jahrling, P.B. et al., "Evaluation of immune globulin and recombinant interferon-alpha2b for treatment of experimental Ebola virus infections", *The Journal of Infectious Diseases*, 179(Suppl 1):S224-S234 (1999).

Miranda, M.B. et al., "Differential activation of apoptosis regulatory pathways during monocytic vs granulocytic differentiation: a requirement for Bcl-X(L)and XIAP in the prolonged survival of monocytic cells", *Journal of the Leukemia Society of America*, 17(2):1157-79 (2001).

Peters, C.J. and Ledue, J.W., "An introduction to Ebola: the virus and the disease", *The Journal of Infectious Diseases*, 179(Suppl 1):ix-xvi (1999).

Sanchez, A. et al., "Sequence analysis of the Ebola virus genome: organization, genetic elements, and comparison with the genome of Marburg virus", *Virus Research*, 29(3):215-240 (1993).

Shabbits, J.A. et al., "Tumor chemosensitization strategies based on apoptosis manipulations", *Molecular Cancer Therapeuctics*, 2(8):805-813 (2003).

Vlasov et al., "Inhibition of the Influenza Virus M Protein mRNA Transaltion in vitro with Complementary Oligonucleotides", *Nucleosides & Nucleotides*, 10(1-3):649-650 (1991).

Warfield, K.I. et al., "Role of natural killer cells in innate protection against lethal ebola virus infection", *The Journal of Experimental Medicine*, 200(2):169-179 (2004).

Callahan, P.L. et al. "Molecular cloning and complete sequence determination of RNA genome of human rhinovirus type 14", *Proc. Natl. Acad. Sci. U.S.A.*, 82(3):732-736 (1985).

Crooke, R.M. et al. "In vitro toxicological evaluation of ISIS 1082, a phosphorothioate oligonucleotide inhibitor of herpes simplex virus", *Antimicrobial Agents and Chemotherapy*, 36(3):527-532 (1992).

Faria, M. et al., "Phosphoramidate oligonucleotides as potent antisense molecules in cells and in vivo", *Nature Biotechnology*, 19(1):40-44 (2001).

Kinney et al., "Inhibition of dengue virus serotypes 1 to 4 in vero cell cultures with morpholino oligomers", *Journal of Virology*, 79:5116-5128 (2005).

Lee, W-M. et al., "Complete sequence of the RNA genome of human rhinovirus 16, a clinically useful common cold virus belonging to the ICAM-1 receptor group", *Virus Genes*, 9(2):177-184 (1994).

Mizuta, T. et al., "Antisense oligonucleotides directed against the viral RNA polymerase gene enhance survival of mice infected with influenza A", *Nature Biotechnology*, 17(6):583-587 (1999).

NCBI Genbank Nucleotide Accession No. AF091736, VESV-like calicivirus strain Pan-1, complete genome, 5 pages (1998).

NCBI Genbank Nucleotide Accession No. AF169005, Hepatitis C virus subtype 2a isolate NDM59, complete genome, 5 pages (1999).

Robaczewska, M. et al., "Inhibition of hepadnaviral replication by polyethylenimine-based intravenous delivery of antisense phosphodiester oligodeoxynucleotides to the liver.", *Nature Publishingucleic Acids Res.*, 31(13):3406-15 (2003).

Sosnovtsev, S. and Green K.Y, "RNA transcripts derived from a cloned full-length copy of the feline calicivirus genome do not require VpG for infectivity", *Virology*, 210:383-390 (1995).

Abe et al., "Antisense therapy of influenza," *European Journal of Pharmaceutical Sciences* 13:61-69, 2001.

Abe et al., "Inhibition of Influenza Virus Replication by Phosphorothioate and Liposomally Endocapsulated Oligonucleotides," *Nucleosides & Nucleotides* 17(1-3):471-478, 1998.

Abe et al., "Specific inhibition of influenza virus RNA polymerase and nucleoprotein gene expression by liposomally encapsulated antisense phosphorothioate oligonucleotides in MDCK cells," *Antiviral Chemistry & Chemotherapy* 9(3):253-262, 1998.

Huffman et al., "Influenza Virus-Inhibitory Activity of a Series of Antisense Oligonucleotides (Abstract)," *Antiviral Research* 20:152, 1993.

Moulton et al., "HIV Tat Peptide Enhances Cellular Delivery of Antisense Morpholino Oligomers," *Antisense and Nucleic Acid Drug Development* 13:31-43, 2003.

Moulton et al., "Peptide-assisted delivery of Steric-blocking antisense oligomers," *Current Opinion in Molecular Therapeutics* 5(2):123-132, 2003.

Database WPI Week 199942 Abstract, Thomson Scientific, Jun. 16, 1999.

* cited by examiner

(-)NP-3 'trm (SEQ ID NO:13)

H5N1 (34 isolates)

$A_{100}G_{100}C_{100}A_{100}A_{100}A_{100}A_{100}G_{100}C_{100}A_{100}G_{100}G_{100}G_{97}T_{100}A_{97}G_{97}A_{100}T_{100}A_{100}A_{100}T_{100}C_{100}$

H1N1 (68 isolates)

$A_{100}G_{100}C_{100}A_{100}A_{100}A_{100}A_{100}G_{100}C_{100}A_{100}G_{100}G_{100}G_{100}T_{100}A_{96}G_{97}A_{100}T_{100}A_{100}A_{100}T_{100}C_{100}$

PB1-AUG (SEQ ID NO:12)

H5N1 (26 isolates)

$G_{100}A_{100}C_{100}A_{100}T_{100}C_{100}C_{100}A_{100}T_{100}T_{100}C_{100}A_{100}A_{100}A_{96}T_{100}G_{100}G_{100}T_{96}T_{100}T_{100}G_{100}$

H1N1 (17 isolates)

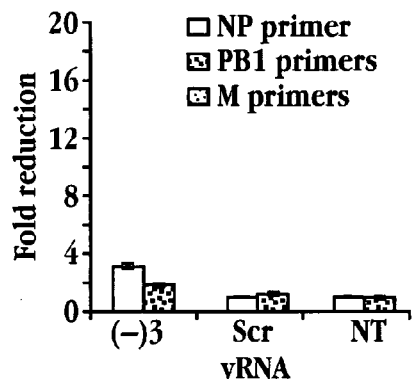
Fig. 8A
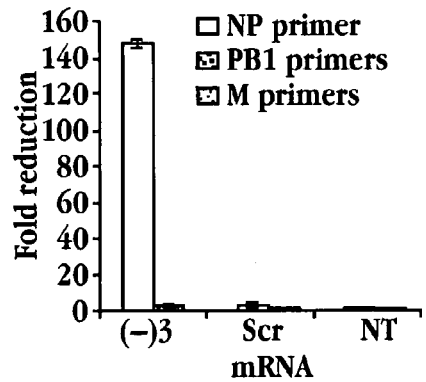
Fig. 8B
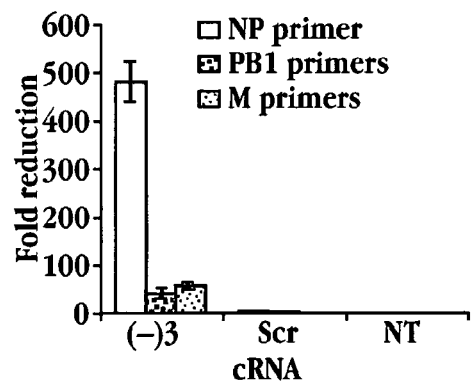
Fig. 8C
Step 1:
PMO incubation →6h→ Virus infection MOI=0.05 →3h→ Supernatant collection Virus titer measurement
Step 2:
RNA species-specific reverse transcription ⟶ Q-PCR
Fig. 8D

SEQUENCE LISTING

```
<160> NUMBER OF SEQ ID NOS: 35

<210> SEQ ID NO 1
<211> LENGTH: 50
<212> TYPE: RNA
<213> ORGANISM: Influenza A virus

<400> SEQUENCE: 1
ucacucacug agugacauca aaaucauggc gucccaaggc accaaacggu        50

<210> SEQ ID NO 2
<211> LENGTH: 50
<212> TYPE: RNA
<213> ORGANISM: Influenza A virus

<400> SEQUENCE: 2
agcgaaagca ggucaauuau auucaauaug gaaagaauaa aagaacuaag        50

<210> SEQ ID NO 3
<211> LENGTH: 50
<212> TYPE: RNA
<213> ORGANISM: Influenza A virus

<400> SEQUENCE: 3
agcgaaagca ggcaaaccau uugaauggau gucaauccga ccuuacuuuu        50

<210> SEQ ID NO 4
<211> LENGTH: 25
<212> TYPE: RNA
<213> ORGANISM: Influenza A virus

<400> SEQUENCE: 4
aaagaaaaau acccuuguuu cuacu                                   25

<210> SEQ ID NO 5
<211> LENGTH: 25
<212> TYPE: RNA
<213> ORGANISM: Influenza A virus

<400> SEQUENCE: 5
agcaaaagca ggguagauaa ucacu                                   25
```

```
<210> SEQ ID NO 6
<211> LENGTH: 25
<212> TYPE: RNA
<213> ORGANISM: Influenza A virus

<400> SEQUENCE: 6
caugaaaaaa ugccuuguuc cuacu                                              25

<210> SEQ ID NO 7
<211> LENGTH: 25
<212> TYPE: RNA
<213> ORGANISM: Influenza A virus

<400> SEQUENCE: 7
agcgaaagca ggcaaaccau uugaa                                              25

<210> SEQ ID NO 8
<211> LENGTH: 25
<212> TYPE: RNA
<213> ORGANISM: Influenza A virus

<400> SEQUENCE: 8
guuuaaaaac gaccuuguuu cuacu                                              25

<210> SEQ ID NO 9
<211> LENGTH: 25
<212> TYPE: RNA
<213> ORGANISM: Influenza A virus

<400> SEQUENCE: 9
agcgaaagca ggucaauuau auuca                                              25

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 10
cttgggacgc catgattttg                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 11
cttttattct ttccatattg                                                    20

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 12
gacatccatt caaatggttt g                                                  21

<210> SEQ ID NO 13
<211> LENGTH: 22
```

```
<212> TYPE: DNA
<213> ORGANISM: Artificial Sequence
<220> FEATURE:
<223> OTHER INFORMATION: Synthetic Oligomer

<400> SEQUENCE: 13
agcaaaagca gggtagataa tc                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 14
gaaaaatacc cttgtttcta ct                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 15
agtagaaaca agggtatttt tc                                              22

<210> SEQ ID NO 16
<211> LENGTH: 12
<212> TYPE: DNA
<213> ORGANISM: Artificial Sequence
<220> FEATURE:
<223> OTHER INFORMATION: Synthetic Oligomer

<400> SEQUENCE: 16
agcaaaagca gg                                                         12

<210> SEQ ID NO 17
<211> LENGTH: 13
<212> TYPE: DNA
<213> ORGANISM: Artificial Sequence
<220> FEATURE:
<223> OTHER INFORMATION: Synthetic Oligomer

<400> SEQUENCE: 17
agtagaaaca agg                                                        13

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 18
agcgaaagca ggcaaaccat                                                 20

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 19 gaaaaatgc cttgttccta ct                                               22
```

-continued

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 20
agtaggaaca aggcattttt tc                                           22

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 21
agcgaaagca ggtcaattat                                              20

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 22
taaaaacgac cttgtttcta ct                                           22

<210> SEQ ID NO 23
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 23
agtagaaaca aggtcgtttt ta                                           22

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 24
agtctcgact tgctacctca                                              20

<210> SEQ ID NO 25
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 25

Arg Arg Arg Arg Arg Phe Phe Arg Arg Arg Arg Cys
1               5                   10

<210> SEQ ID NO 26
<211> LENGTH: 14
<212> TYPE: PRT
<213> ORGANISM: Artificial Sequence
<220> FEATURE:

```
<223> OTHER INFORMATION: Synthetic arginine-rich peptide
<220> FEATURE:
<221> NAME/KEY: VARIANT
<222> LOCATION: (2)..(13)
<223> OTHER INFORMATION: Xaa = 6-aminohexanoic acid
<220> FEATURE:
<221> NAME/KEY: VARIANT
<222> LOCATION: (14)..(14)
<223> OTHER INFORMATION: Xaa = beta-Alanine

<400> SEQUENCE: 26

Arg Xaa Arg Arg Xaa Arg Arg Xaa Arg Arg Xaa Arg Xaa Xaa
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: VARIANT
<222> LOCATION: (2)..(16)
<223> OTHER INFORMATION: Xaa = 6-aminohexanoic acid
<220> FEATURE:
<221> NAME/KEY: VARIANT
<222> LOCATION: (17)..(17)
<223> OTHER INFORMATION: Xaa = beta-Alanine

<400> SEQUENCE: 27

Arg Xaa Arg Xaa Arg Xaa Arg Xaa Arg Xaa Arg Xaa Arg Xaa Arg Xaa
1               5                   10                  15

Xaa

<210> SEQ ID NO 28
<211> LENGTH: 9
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: VARIANT
<222> LOCATION: (2)..(8)
<223> OTHER INFORMATION: Xaa = 6-aminohexanoic acid
<220> FEATURE:
<221> NAME/KEY: VARIANT
<222> LOCATION: (9)..(9)
<223> OTHER INFORMATION: Xaa = beta-Alanine

<400> SEQUENCE: 28

Arg Xaa Arg Xaa Arg Xaa Arg Xaa Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: VARIANT
<222> LOCATION: (2)..(7)
<223> OTHER INFORMATION: Xaa = 6-aminohexanoic acid
<220> FEATURE:
<221> NAME/KEY: VARIANT
<222> LOCATION: (8)..(8)
<223> OTHER INFORMATION: Xaa = beta-Alanine

<400> SEQUENCE: 29

Arg Xaa Arg Arg Xaa Arg Xaa Xaa
1               5
```

```
<210> SEQ ID NO 30
<211> LENGTH: 11
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: VARIANT
<222> LOCATION: (2)..(10)
<223> OTHER INFORMATION: Xaa = 6-aminohexanoic acid
<220> FEATURE:
<221> NAME/KEY: VARIANT
<222> LOCATION: (11)..(11)
<223> OTHER INFORMATION: Xaa = beta-Alanine

<400> SEQUENCE: 30

Arg Xaa Arg Arg Xaa Arg Arg Xaa Arg Xaa Xaa
1               5                   10

<210> SEQ ID NO 31
<211> LENGTH: 12
<212> TYPE: RNA
<213> ORGANISM: Influenza A

<400> SEQUENCE: 31
ccugcuuucg cu                                                           12

<210> SEQ ID NO 32
<211> LENGTH: 13
<212> TYPE: RNA
<213> ORGANISM: Influenza A

<400> SEQUENCE: 32
aguagaaaca agg                                                          13

<210> SEQ ID NO 33
<211> LENGTH: 12
<212> TYPE: RNA
<213> ORGANISM: Influenza A

<400> SEQUENCE: 33
agcgaaagca gg                                                           12

<210> SEQ ID NO 34
<211> LENGTH: 12
<212> TYPE: RNA
<213> ORGANISM: Influenza A

<400> SEQUENCE: 34
agcgaaagca gg                                                           12

<210> SEQ ID NO 35
<211> LENGTH: 13
<212> TYPE: RNA
<213> ORGANISM: Influenza A

<400> SEQUENCE: 35
ccuuguuucu acu                                                          13
```

ANTISENSE ANTIVIRAL COMPOUND AND METHOD FOR TREATING INFLUENZA VIRAL INFECTION

This application claims priority to U.S. provisional patent application No. 60/622,077 filed Oct. 26, 2004, which is incorporated herein in its entirety by reference.

STATEMENT OF GOVERNMENT INTEREST

This invention was made with government support under grant number R01 AI056267 awarded by the National Institutes of Health. The government has certain rights in this invention.

FIELD OF THE INVENTION

The invention relates to antisense oligonucleotide compounds for use in treating an influenza virus infection and antiviral treatment methods employing the compounds.

REFERENCES

Agrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Cox, N. J. and K. Subbarao (1999). "Influenza." *Lancet* 354 (9186): 1277-82.

Cox, N. J. and K. Subbarao (2000). "Global epidemiology of influenza: past and present." *Annu Rev Med* 51: 407-21.

Cross, C. W., J. S. Rice, et al. (1997). "Solution structure of an RNA×DNA hybrid duplex containing a 3'-thioformacetal linker and an RNA A-tract." *Biochemistry* 36(14): 4096-107.

Dagle, J. M., J. L. Littig, et al. (2000). "Targeted elimination of zygotic messages in *Xenopus laevis* embryos by modified oligonucleotides possessing terminal cationic linkages." *Nucleic Acids Res* 28(10): 2153-7.

Ding, D., S. M. Grayaznov, et al. (1996). "An oligodeoxyribonucleotide N3'-->P5' phosphoramidate duplex forms an A-type helix in solution." *Nucleic Acids Res* 24(2): 354-60.

Egholm, M., O. Buchardt, et al. (1993). "PNA hybridizes to complementary oligonucleotides obeying the Watson-Crick hydrogen-bonding rules." *Nature* 365(6446): 566-8.

Felgner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* 0(14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl) carbonate, and 3'-(5-fluoro-2'-deoxyuridinyl) 5'-thymidinyl carbonate." *J Med Chem* 12(1): 154-7.

Moulton, H. M., M. H. Nelson, et al. (2004). "Cellular uptake of antisense morpholino oligomers conjugated to arginine-rich peptides." *Bioconjug Chem* 15(2): 290-9.

Nelson, M. H., D. A. Stein, et al. (2005). "Arginine-rich peptide conjugation to morpholino oligomers: effects on antisense activity and specificity." *Bioconjug Chem* 16(4): 959-66.

Strauss, J. H. and E. G. Strauss (2002). *Viruses and Human Disease*. San Diego, Academic Press.

Summerton, J. and D. Weller (1997). "Morpholino antisense oligomers: design, preparation, and properties." *Antisense Nucleic Acid Drug Dev* 7(3): 187-95.

Toulme, J. J., R. L. Tinevez, et al. (1996). "Targeting RNA structures by antisense oligonucleotides." *Biochimie* 78(7): 663-73.

Williams, A. S., J. P. Camilleri, et al. (1996). "A single intra-articular injection of liposomally conjugated methotrexate suppresses joint inflammation in rat antigen-induced arthritis." *Br J Rheumatol* 35(8): 719-24.

Wu, G. Y. and C. H. Wu (1987). "Receptor-mediated in vitro gene transformation by a soluble DNA carrier system." *J Biol Chem* 262(10): 4429-32.

BACKGROUND OF THE INVENTION

Influenza viruses have been a major cause of human mortality and morbidity throughout recorded history. Influenza A virus infection causes millions of cases of severe illness and as many as 500,000 deaths each year worldwide. Epidemics vary widely in severity but occur at regular intervals and always cause significant mortality and morbidity, most frequently in the elderly population. Although vaccines against matched influenza strains can prevent illness in 60-80% of healthy adults, the rate of protection is much lower in high-risk groups. Furthermore, vaccination does not provide protection against unexpected strains, such as the H5 and H7 avian influenza outbreaks in Hong Kong in 1997 and Europe and Southeast Asia in 2003 and 2004. Current anti-influenza drugs are limited in their capacity to provide protection and therapeutic effect (Cox and Subbarao 1999; Cox and Subbarao 2000).

Influenza A is a segmented RNA virus of negative-polarity. Genome segments are replicated by a complex of 4 proteins: the 3 polymerase polypeptides (PA, PB1 and PB2) and NP (Nucleoprotein). The 5' and 3' terminal sequence regions of all 8 genome segments are highly conserved within a genotype (Strauss and Strauss 2002).

Influenza A viruses can be subtyped according to the antigenic and genetic nature of their surface glycoproteins; 15 hemagglutinin (HA) and 9 neuraminidase (NA) subtypes have been identified to date. Viruses bearing all known HA and NA subtypes have been isolated from avian hosts, but only viruses of the H1N1 (1918), H2N2 (1957/58), and H3N2

(1968) subtypes have been associated with widespread epidemics in humans (Strauss and Strauss 2002).

Since 1997, when H5N1 influenza virus was transmitted to humans and killed 6 of 18 infected persons, there have been multiple transmissions of avian influenza viruses to mammals. Either the whole virus is transmitted directly or gene segments from the avian influenza virus are acquired by mammalian strains. Widespread infections of poultry with H5N1 viruses in Asia have caused increasing concern that this subtype may achieve human-to-human spread and establish interspecies transmission. The species which different types of influenza viruses are able to infect are determined by different forms of the virus glycoproteins (HA, NA). This provides a considerable species barrier between birds and humans which is not easily overcome. Pigs, however, provide a "mixing pot"-able to be infected by both types of virus and thereby allowing the passage of avian viruses to humans. When an individual pig cell is co-infected with both avian and human influenza viruses, recombinant forms can emerge that carry an avian HA genotype but readily infect humans. Avian HA can infect pigs, but not humans. In pigs, during genome segment packaging, it is possible to create a virus with several Avian segments and Human HA and/or NA segments (Cox and Subbarao 2000).

Influenza viruses infect humans and animals (e.g., pigs, birds, horses) and may cause acute respiratory disease. There have been numerous attempts to produce vaccines effective against influenza virus. None, however, have been completely successful, particularly on a long-term basis. This may be due, at least in part, to the segmented characteristic of the influenza virus genome, which makes it possible, through re-assortment of the segments, for numerous forms to exist. For example, it has been suggested that there could be an interchange of RNA segments between animal and human influenza viruses, which would result in the introduction of new antigenic subtypes into both populations. Thus, a long-term vaccination approach has failed, due to the emergence of new subtypes (antigenic "shift"). In addition, the surface proteins of the virus, hemagglutinin and neuraminidase, constantly undergo minor antigenic changes (antigenic "drift"). This high degree of variation explains why specific immunity developed against a particular influenza virus does not establish protection against new variants. Hence, alternative antiviral strategies are needed. Although influenza B and C viruses cause less clinical disease than the A types, new antiviral drugs should also be helpful in curbing infections caused by these agents.

Influenza viruses that occur naturally among birds are called avian influenza (bird flu). The birds carry the viruses in their intestines but do not generally get sick from the infection. However, migratory birds can carry the bird flu to infect domestic chickens, ducks and turkeys causing illness and even death. Avian flu does not easily infect humans but when human exposure is more frequent, such as contact with domestic birds, human infections occur. A dangerous bird flu (H5N1) was first identified in terns in South Africa in 1961 and was identified as a potentially deadly form of flu. Outbreaks of H5N1 occurred in eight Asian countries in late 2003 and 2004. At that time more than 100 million birds in these countries either died or were killed in order to control the outbreak. Beginning in June of 2004 new deadly outbreaks of H5N1 were reported in Asia which is currently ongoing. Human infections of H5N1 have been observed in Thailand, Vietnam and Cambodia with a death rate of about 50 percent. These infections have mostly occurred from human contact with infected poultry but a few cases of human-to-human spread of H5N1 have occurred.

Currently, there is no vaccine to protect humans against H5N1 but research efforts are underway. There are four currently approved influenza medications, amantadine, rimantadine, oseltamivir and zanamivir. Unfortunately, the H5N1 virus is resistant to both amantadine and rimantidine. The remaining oseltamivir and zanamivir may show some efficacy to H5N1 but need to be evaluated more extensively.

In view of the severity of the diseases caused by influenza viruses there is an immediate need for new therapies to treat influenza infection. Given the lack of effective prevention or therapies, it is therefore an object of the present invention to provide therapeutic compounds and methods for treating a host infected with an influenza virus.

SUMMARY OF THE INVENTION

The invention includes, in one aspect, an anti-viral compound effective in inhibiting replication within a host cell of an RNA virus having a single-stranded, negative sense genome and selected from the Orthomyxoviridae family including the Influenzavirus A, Influenzavirus B and Influenzavirus C genera. The compound targets viral RNA sequences within a region selected from the following: 1) the 5' or 3' terminal 25 bases of the negative sense viral RNA segments; 2) the terminal 25 bases of the 3' terminus of the positive sense cRNA and; 3) 50 bases surrounding the AUG start codons of influenza viral mRNAs.

The antiviral compound consists of an oligonucleotide analog characterized by: a) a nuclease-resistant backbone, b) 12-40 nucleotide bases, and c) a targeting sequence of at least 12 bases in length, that hybridizes to a target region selected from the following: i) the 5' or 3' terminal 25 bases of a negative sense viral RNA segment of Influenzavirus A, Influenzavirus B and Influenzavirus C, ii) the terminal 30 bases of the 3' terminus of a positive sense cRNA of Influenzavirus A, Influenzavirus B and Influenzavirus C, and iii) the 50 bases surrounding the AUG start codon of an influenza viral mRNA.

The oligonucleotide analog also has: a) the capability of being actively taken up by mammalian host cells, and b) the ability to form a heteroduplex structure with the viral target region, wherein said heteroduplex structure is: i) composed of the positive or negative sense strand of the virus and the oligonucleotide compound, and ii) characterized by a Tm of dissociation of at least 45° C.

The invention includes, in another aspect, an antiviral compound that inhibits, in a mammalian host cell, replication of an infecting influenza virus having a single-stranded, segmented, negative-sense genome and selected from the Orthomyxoviridae family. The compound is administered to the infected host cells as an oligonucleotide analog characterized by the elements described above on pp. 5-6. The compound may be administered to a mammalian subject infected with the influenza virus, or at risk of infection with the influenza virus.

The compound may be composed of morpholino subunits linked by uncharged, phosphorus-containing intersubunit linkages, joining a morpholino nitrogen of one subunit to a 5' exocyclic carbon of an adjacent subunit. In one embodiment, the intersubunit linkages are phosphorodiamidate linkages, such as those having the structure:

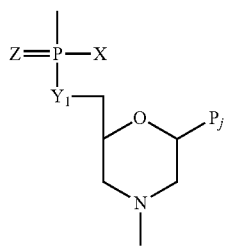

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino, e.g., wherein X=$NR_2$, where each R is independently hydrogen or methyl.

The compound may be a covalent conjugate of an oligonucleotide analog moiety capable of forming such a heteroduplex structure with the positive or negative sense strand of the virus, and an arginine-rich polypeptide effective to enhance the uptake of the compound into host cells. Exemplary polypeptides have one of the sequences identified as SEQ ID NOs:25-30.

In a related aspect, the invention includes a heteroduplex complex formed between:
(a) the 5' or 3' terminal 25 bases of the negative sense viral RNA and/or;
(b) the terminal 25 bases of the 3' terminus of the positive sense mRNA and/or;
(c) 50 bases surrounding the AUG start codons of viral mRNA of an influenza virus selected from the Orthomyxoviridae family and,
(d) an oligonucleotide analog compound characterized by:
  (i) a nuclease-resistant backbone,
  (ii) capable of uptake by mammalian host cells,
  (iii) containing between 12-40 nucleotide bases,
where said heteroduplex complex has a Tm of dissociation of at least 45° C. and disruption of a stem-loop secondary structure.

An exemplary oligonucleotide analog is composed of morpholino subunits linked by uncharged, phosphorus-containing intersubunit linkages, joining a morpholino nitrogen of one subunit to a 5' exocyclic carbon of an adjacent subunit. The compound may have phosphorodiamidate linkages, such as in the structure

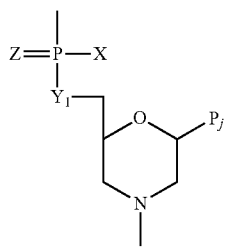

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino. In a preferred compound, X=$NR_2$, where each R is independently hydrogen or methyl. The compound may be the oligonucleotide analog alone or a conjugate of the analog and an arginine-rich polypeptide capable of enhancing the uptake of the compound into host cells. Exemplary polypeptides have one of the sequences identified as SEQ ID NOs:25-30.

In still another aspect, the invention includes an oligonucleotide analog compound for use in inhibiting replication in mammalian host cells of an influenza virus having a single-stranded, segmented, negative-sense RNA genome and selected from the Orthomyxoviridae family. The compound is characterized by the elements described above on pp. 5-6.

An exemplary oligonucleotide analog is composed of morpholino subunits linked by uncharged, phosphorus-containing intersubunit linkages, joining a morpholino nitrogen of one subunit to a 5' exocyclic carbon of an adjacent subunit. The compound may have phosphorodiamidate linkages, such as in the structure

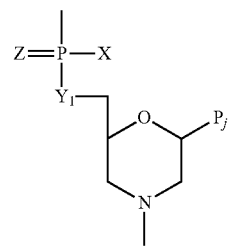

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino. In a preferred compound, X=$NR_2$, where each R is independently hydrogen or methyl. The compound may be the oligonucleotide analog alone or a conjugate of the analog and an arginine-rich polypeptide capable of enhancing the uptake of the compound into host cells. Exemplary polypeptides have one of the sequences identified as SEQ ID NOs:25-30.

For treatment of Influenza A virus as given below, the targeting sequence hybridizes to a region associated with one of the group of sequences identified as SEQ ID NOs:1-9. Preferred targeting sequences are those complementary to either the minus strand target of SEQ ID NO:4 or the positive-strand target of SEQ ID NO:3. Exemplary antisense phosphorodiamidate morpholino oligomers ("PMOs") that target these two regions are listed as SEQ ID NOs:12 and 13, respectively.

BRIEF DESCRIPTION OF THE FIGURES

FIG. 4 shows the conservation of target sequences in two important stereotypes of influenza, H1N1 and H5N1, for each base of two preferred PMOs (PB1-AUG and NP-3' terminus; SEQ ID NOs:13 and 12). The percentage of isolates having the indicated base is the subscript number after each base.

FIGS. 8A-8C show the suppression of transcription of vRNA to mRNA and cRNA by PMOs that target the 3' terminus of NP vRNA. FIG. 8D describes the experimental protocol.

DETAILED DESCRIPTION OF THE INVENTION

I. Definitions

Figure 1A:
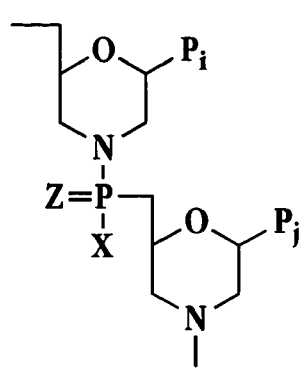
FIGS. 1A-1D show the repeating subunit segment of several preferred morpholino oligonucleotides, designated A through D, constructed using subunits having 5-atom (A), six-atom (B) and seven-atom (C-D) linking groups suitable for forming polymers.

The terms below, as used herein, have the following meanings, unless indicated otherwise:

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_1$ to $C_4$ alkyl.

"Alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl".

"Aryl" refers to a substituted or unsubstituted monovalent aromatic radical, generally having a single ring (e.g., benzene) or two condensed rings (e.g., naphthyl). This term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl. Preferred substituents include halogen, methyl, ethyl, and methoxy. Generally preferred are aryl groups having a single ring.

"Aralkyl" refers to an alkyl, preferably lower ($C_1$-$C_4$, more preferably $C_1$-$C_2$) alkyl, substituent which is further substituted with an aryl group; examples are benzyl (—$CH_2C_6H_5$) and phenethyl (—$CH_2CH_2C_6H_5$).

"Heterocycle" refers to a non-aromatic ring, preferably a 5- to 7-membered ring, whose ring atoms are selected from the group consisting of carbon, nitrogen, oxygen and sulfur. Preferably, the ring atoms include 3 to 6 carbon atoms. Such heterocycles include, for example, pyrrolidine, piperidine, piperazine, and morpholine.

The term "substituted", with respect to an alkyl, alkenyl, alkynyl, aryl, aralkyl, or alkaryl group, refers to replacement of a hydrogen atom with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic.

The terms "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. The analog supports bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 60-100%, are uncharged at physiological pH, and contain a single phosphorous atom. The analog contains between 8 and 40 subunits, typically about 8-25 subunits, and preferably about 12 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A "morpholino oligonucleotide analog" is an oligonucleotide analog composed of morpholino subunit structures of the form shown in FIGS. 1A-1D, where (i) the structures are linked together by phosphorus-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, all of which are incorporated herein by reference.

Figure 1B:
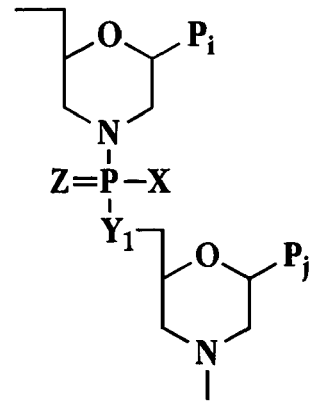

The subunit and linkage shown in FIG. 1B are used for six-atom repeating-unit backbones, as shown in FIG. 1B (where the six atoms include: a morpholino nitrogen, the connected phosphorus atom, the atom (usually oxygen) linking the phosphorus atom to the 5' exocyclic carbon, the 5' exocyclic carbon, and two carbon atoms of the next morpholino ring). In these structures, the atom $Y_1$ linking the 5' exocyclic morpholino carbon to the phosphorus group may be sulfur, nitrogen, carbon or, preferably, oxygen. The X moiety pendant from the phosphorus is any stable group which does not interfere with base-specific hydrogen bonding. Preferred X groups include fluoro, alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures such as shown in FIG. 1B, where X=$NH_2$, NHR, or $NR_2$ (where R is lower alkyl, preferably methyl), Y=O, and Z=O, and $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 1B, X=lower alkoxy, such as methoxy or ethoxy, Y=NH or NR, where R is lower alkyl, and Z=O.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target", relative to the viral genomic RNA, refers to a viral genomic RNA, and specifically, to a region associated with stem-loop secondary structure within the 5'-terminal end 40 bases of the positive-sense RNA strand of a single-stranded RNA (ssRNA) virus described herein.

The term "target sequence" refers to a portion of the target RNA against which the oligonucleotide analog is directed, that is, the sequence to which the oligonucleotide analog will hybridize by Watson-Crick base pairing of a complementary sequence. As will be seen, the target sequence may be a contiguous region of the viral positive-strand RNA, or may be composed of complementary fragments of both the 5' and 3' sequences involved in secondary structure.

The term "targeting sequence" is the sequence in the oligonucleotide analog that is complementary (meaning, in addition, substantially complementary) to the target sequence in the RNA genome. The entire sequence, or only a portion, of the analog compound may be complementary to the target sequence. For example, in an analog having 20 bases, only 12-14 may be targeting sequences. Typically, the targeting sequence is formed of contiguous bases in the analog, but may alternatively be formed of non-contiguous sequences that when placed together, e.g., from opposite ends of the analog, constitute sequence that spans the target sequence. As will be seen, the target and targeting sequences are selected such that binding of the analog is to a region within; 1) the 5' or 3' terminal 25 bases of the negative sense viral RNA; 2) the terminal 25 bases of the 3' terminus of the positive sense mRNA and/or; 3) 50 bases surrounding the AUG start codons of viral mRNA.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

An oligonucleotide analog "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAseH, which are capable of cutting double-stranded RNA/RNA or RNA/DNA complexes.

A "base-specific intracellular binding event involving a target RNA" refers to the specific binding of an oligonucleotide analog to a target RNA sequence inside a cell. The base specificity of such binding is sequence specific. For example, a single-stranded polynucleotide can specifically bind to a single-stranded polynucleotide that is complementary in sequence.

An "effective amount" of an antisense oligomer, targeted against an infecting influenza virus, is an amount effective to reduce the rate of replication of the infecting virus, and/or viral load, and/or symptoms associated with the viral infection.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide analog preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. The analog may also be conjugated, e.g., at its 5' or 3' end, to an arginine-rich peptide, such as a portion of the HIV TAT protein, polyarginine, or to combinations of arginine and other amino acids including the non-natural amino acids 6-aminohexanoic acid (Ahx) and beta-alanine (βAla). Exemplary arginine-rich delivery peptides are listed as SEQ ID NOs:25-30. These exemplary arginine-rich delivery peptides facilitate transport into the target host cell as described (Moulton, Nelson et al. 2004; Nelson, Stein et al. 2005).

Rules for the selection of targeting sequences capable of inhibiting replication of the influenza viral genome are discussed below.

II. Targeted Viruses

The present invention is based on the discovery that effective inhibition of single-stranded, segmented, negative-sense RNA viruses can be achieved by exposing cells infected with influenza virus to antisense oligonucleotide analog compounds (i) that target 1) the 5' or 3' terminal 25 bases of the negative sense viral RNA; 2) the terminal 25 bases of the 3' terminus of the positive sense mRNA and/or; 3) 50 bases surrounding the AUG start codons of viral mRNA; and (ii) having physical and pharmacokinetic features which allow effective interaction between the antisense compound and the virus within host cells. In one aspect, the oligomers can be used in treating a mammalian subject infected with influenza virus.

Figure 3:
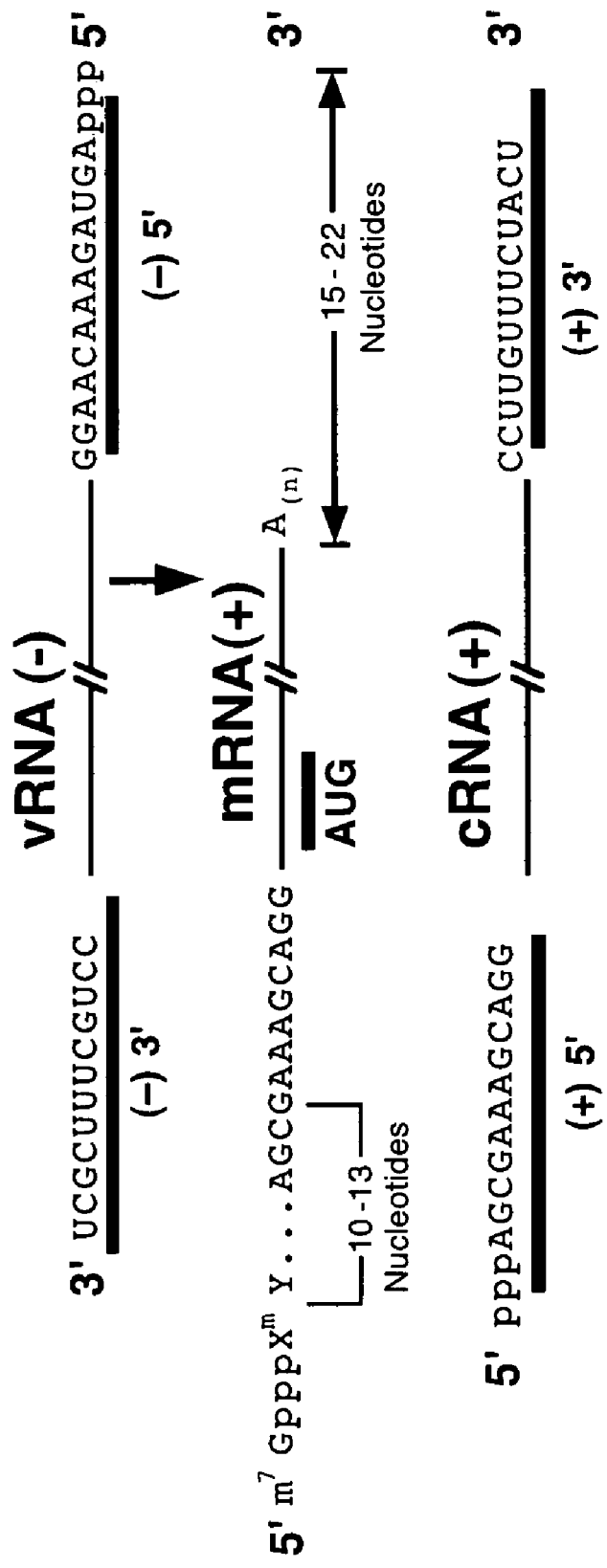
FIG. 3 shows the three different species of influenza virus RNA present in infected cells, vRNA, mRNA and cRNA, and the target location of targeting PMO described herein. The 3' arm of vRNA(-) depicted corresponds to SEQ ID NO:31. The 5' arm of the vRNA(-) depicted corresponds to SEQ ID NO:32. The 5' arm of mRNA depicted corresponds to SEQ ID NO:33. The 5' arm of cRNA(+) depicted corresponds to SEQ ID NO:34. The 3' arm of the cRNA(+) depicted corresponds to SEQ ID NO:35.

The invention targets RNA viruses having genomes that are: (i) single stranded, (ii) segmented and (iii) negative polarity. The targeted viruses also synthesize two different versions of a genomic complement of the negative sense virion RNA (vRNA) with positive polarity: 1) cRNA that is used as a template for replication of negative sense virion RNA, and 2) a complementary positive sense RNA (mRNA) that is used for translation of viral proteins. FIG. 3 is a schematic that shows these different RNA species and the target location of antisense PMO described in the present invention. In particular, targeted viral families include members of the Orthomyxoviridae family including the Influenzavirus A, Influenzavirus B and Influenzavirus C genera. Various physical, morphological, and biological characteristics of members of the Orthomyxoviridae family can be found, for example, in Textbook of Human Virology, R. Belshe, ed., 2$^{nd}$ Edition, Mosby, 1991, at the Universal Virus Database of the International Committee on Taxonomy of Viruses (www.ncbi.nlm-.nih.gov/ICTVdb/index.htm) and in human virology textbooks (see, for example (Strauss and Strauss 2002). Some of the key biological characteristics of the Orthomxyoviridae family of viruses are described below.

Influenza Viruses

Influenza A, influenza B and influenza C viruses are the only members of the Influenzavirus A, Influenzavirus B and Influenzavirus C genera, respectively. These viruses are membrane-enclosed viruses whose genomes are segmented negative-sense (i.e. minus) strands of RNA ((−)RNA). The ten influenza virus genes are present on eight segments of the single-stranded RNA of strains A and B, and on seven segments of strain C. The segments vary in size (from 890 to 2341 nucleotides in length) and each is a template for synthesis of different mRNAs. The influenza virus virion contains virus-specific RNA polymerases necessary for mRNA synthesis from these templates and, in the absence of such specific polymerases, the minus strand of influenza virus RNA is not infectious. Initiation of transcription of the mRNAs occurs when the influenza virus mRNA polymerase takes 12 to 15 nucleotides from the 5' end of a cellular mRNA or mRNA precursor and uses the borrowed oligonucleotide as a primer. This process has been termed "cap-snatching" because it places a 5' cap structure on the viral mRNA. Generally, the mRNAs made through this process encode only one protein. The M gene and NS gene viral RNA segments also code for spliced mRNAs, which results in production of two different proteins for each of these two segments.

Replication of influenza viral RNA occurs in the nucleus and involves the synthesis of three different species of RNA. A schematic of this process is shown in FIG. 3. After infection of a naïve cell, the minus strand virion RNA (vRNA) is transported to the nucleus where RNA destined for translation (mRNA) is synthesized using 5'-terminal 10-13 nucleotide primers cleaved by viral-encoded enzymes from capped cellular pre-mRNA molecules (i.e. cap-snatching). Synthesis of each mRNA continues to near the end of the genome segment where an oligo(U) stretch is encountered and a poly(A) tail is added. The dedicated viral mRNAs are transported to the cytoplasm for translation and after sufficient viral proteins are transported back into the nucleus, synthesis of vRNA destined for nascent virions is initiated. An exact antigenomic copy of vRNA is synthesized (termed cRNA) which is a perfect complement of the genomic vRNA and serves as a template for production of new vRNA. The different RNAs synthesized during influenza virus replication are shown schematically in FIG. 3.

GenBank references for exemplary viral nucleic acid target sequences representing influenza A genomic segments are listed in Table 1 below. The nucleotide sequence numbers in Table 1 are derived from the Genbank reference for the positive-strand RNA. It will be appreciated that these sequences are only illustrative of other sequences in the Orthomyxoviridae family, as may be available from available gene-sequence databases of literature or patent resources. The sequences below, identified as SEQ ID NOs:1-9, are also listed in the Sequence Listing at the end of the specification.

The target sequences in Table 1 represent; 1) the 5' or 3' terminal 25 bases of the negative sense viral RNA (SEQ ID NOs:4-9); 2) the terminal 25 bases of the 3' terminus of the positive sense mRNA (SEQ ID NOs:4-9) and; 3) 50 bases surrounding the AUG start codons of the indicated influenza virus genes (SEQ ID NOs:1-3). The sequences shown are the positive-strand (i.e., antigenomic or mRNA) sequence in the 5' to 3' orientation. It will be obvious that when the target is the minus-strand vRNA the targeted sequence is the complement of the sequence listed in Table 1.

Table 1 lists the targets for three different influenza A viral genes, PB2, PB1 and nucleoprotein (NP), encoded by genomic segments 1, 2 and 5, respectively. The PB1, PB2 and NP proteins are components of the viral RNA polymerase and PB2 also functions as the "cap-snatching" enzyme. The target sequences for the AUG start codons of the three genes are represented as SEQ ID NOs:1-3. The 3' terminal sequences of the three genomic segments are represented by SEQ ID NOs: 4, 6 and 8 and can be targeted on both the positive strand and the negative strand of those segments. The 5' terminal sequences (SEQ ID NOs:5, 7 and 9) can be successfully targeted on the minus strand.

TABLE 1

Exemplary Influenza Viral Nucleic Acid Target Sequences

| Name | GenBank No. | Nucleotide Region | Sequence (5' to 3') | SEQ ID NO |
|---|---|---|---|---|
| NP-31 | J02147 | 21-70 | UCACUCACUGAGUGACAUCAA AAUCAUGGCGUCCCAAGGCAC CAAACGGU | 1 |
| PB2-11 | V00603 | 1-50 | AGCGAAAGCAGGUCAAUUAUA UUCAAUAUGGAAAGAAUAAAA GAACUAAG | 2 |
| PB1-AUG | J02151 | 1-50 | AGCGAAAGCAGGCAAACCAUU UGAAUGGAUGUCAAUCCGACC UUACUUUU | 3 |
| NP-3'term | J02147 | 1541-1565 | AAAGAAAAAUACCCUUGUUUC UACU | 4 |
| NP-5'term | J02147 | 1-25 | AGCAAAAGCAGGGUAGAUAAU CACU | 5 |
| PB1-3'term | J02151 | 2317-2341 | CAUGAAAAAAUGCCUUGUUCC UACU | 6 |
| PB1-5'term | J02151 | 1-25 | AGCGAAAGCAGGCAAACCAUU UGAA | 7 |
| PB2-3'term | V00603 | 2317-2341 | GUUUAAAAACGACCUUGUUUC UACU | 8 |
| PB2-5'term | V00603 | 1-25 | AGCGAAAGCAGGUCAAUUAUA UUCA | 9 |

FIG. 4 shows conservation of target sequences in two important serotypes of influenza, H1N1 and H5N1, for each base of two preferred PMOs (PB1-AUG and NP-3'term; SEQ ID NOs: 13 and 12) based on Los Alamos National Laboratory (LANL) influenza database of genome sequences (Macken, C., Lu, H., Goodman, J., & Boykin, L., "The value of a database in surveillance and vaccine selection," in *Options for the Control of Influenza IV*. A.D.M.E. Osterhaus, N. Cox & A. W. Hampson (Eds.) Amsterdam: Elsevier Science, 2001, 103-106). The same search was conducted with the National Library of Medicine GenBank database which is composed of different sequences for influenza and virtually identical results were obtained. The capital letter indicates the PMO base and the subscript number next to the base indicates the percent conservation for that base for all the isolates in the database. These data indicate only base positions 15 and 16 show any variation for the 3'(–)NP terminus and even better conservation of sequence in the PB1-AUG target.

Targeting sequences are designed to hybridize to a region of the target sequence as listed in Table 1. Selected targeting sequences can be made shorter, e.g., 12 bases, or longer, e.g., 40 bases, and include a small number of mismatches, as long as the sequence is sufficiently complementary to disrupt the stem structure(s) upon hybridization with the target, and forms with the virus positive-strand, a heteroduplex having a Tm of 45° C. or greater.

More generally, the degree of complementarity between the target and targeting sequence is sufficient to form a stable duplex. The region of complementarity of the antisense oligomers with the target RNA sequence may be as short as 8-11 bases, but is preferably 12-15 bases or more, e.g. 12-20 bases, or 12-25 bases. An antisense oligomer of about 14-15 bases is generally long enough to have a unique complementary sequence in the viral genome. In addition, a minimum length of complementary bases may be required to achieve the requisite binding Tm, as discussed below.

Oligomers as long as 40 bases may be suitable, where at least the minimum number of bases, e.g., 8-11, preferably 12-15 bases, are complementary to the target sequence. In general, however, facilitated or active uptake in cells is optimized at oligomer lengths less than about 30, preferably less than 25, and more preferably 20 or fewer bases. For PMO oligomers, described further below, an optimum balance of binding stability and uptake generally occurs at lengths of 14-22 bases.

The oligomer may be 100% complementary to the viral nucleic acid target sequence, or it may include mismatches, e.g., to accommodate variants, as long as a heteroduplex formed between the oligomer and viral nucleic acid target sequence is sufficiently stable to withstand the action of cellular nucleases and other modes of degradation which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the viral nucleic acid target sequence, it is effective to stably and specifically bind to the target sequence, such that a biological activity of the nucleic acid target, e.g., expression of viral protein(s), is modulated.

The stability of the duplex formed between the oligomer and the target sequence is a function of the binding Tm and the susceptibility of the duplex to cellular enzymatic cleavage. The Tm of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol*. Vol. 154 pp. 94-107. Each antisense oligomer should have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (50° C. or greater) at a length of 20 bases or less are generally preferred over those requiring greater than 20 bases for high Tm values.

Table 2 below shows exemplary targeting sequences, in a 5'-to-3' orientation, that are complementary to influenza A virus. The sequences listed provide a collection of targeting sequences from which targeting sequences may be selected, according to the general class rules discussed above. SEQ ID NOs:10-12, 15, 17, 20, 23 and 24 are antisense to the positive strand (mRNA or cRNA) of the virus whereas SEQ ID NOs: 13, 14, 16, 18, 19, 21 and 22 are antisense to the minus strand (vRNA). Thus, for example, in selecting a target against the 3' terminus of the minus strand of the NP encoding segment (segment 5 of influenza A) SEQ ID NOs:13 or 16, or a portion of either sequence effective to block the function of the 3' terminus of the minus strand can be selected.

TABLE 2

Exemplary Antisense Oligomer Sequences

| PMO | Target Nucleotides | GenBank Acc. No. | Targeting Antisense Oligomer (5' to 3') | SEQ. ID NO. |
|---|---|---|---|---|
| NP-AUG | 39-58 | J02147 | CTTGGGACGCCATGATTTTG | 10 |
| PB2-AUG | 24-43 | V00603 | CTTTTATTCTTTCCATATTG | 11 |
| PB1-AUG | 13-33 | J02151 | GACATCCATTCAAATGGTTTG | 12 |
| (−)NP-3'trm | 1-22 | J02147 | AGCAAAAGCAGGGTAGATAATC | 13 |
| (−)NP-5'trm | 1544-1565 | J02147 | GAAAAATACCCTTGTTTCTACT | 14 |
| (+)NP-3'trm | 1544-1565 | J02147 | AGTAGAAACAAGGGTATTTTTC | 15 |
| Flu(−)3'trm | 1-12 | J02147 | AGCAAAAGCAGG | 16 |
| Flu(+)3'trm | 1553-1565 | J02147 | AGTAGAAACAAGG | 17 |
| (−)PB1-3'trm | 1-20 | J02151 | AGCGAAAGCAGGCAAACCAT | 18 |
| (−)PB1-5'trm | 2320-2341 | J02151 | GAAAAAATGCCTTGTTCCTACT | 19 |
| (+)PB1-3'trm | 2320-2341 | J02151 | AGTAGGAACAAGGCATTTTTC | 20 |
| (−)PB2-3'trm | 1-20 | V00603 | AGCGAAAGCAGGTCAATTAT | 21 |
| (−)PB2-5'trm | 2320-2341 | V00603 | TAAAAACGACCTTGTTTCTACT | 22 |
| (+)PB2-3'trm | 2320-2341 | V00603 | AGTAGAAACAAGGTCGTTTTA | 23 |
| (+)NP-5'trm | 1-20 | J02147 | AGTCTCGACTTGCTACCTCA | 24 |

III. Antisense Oligonucleotide Analog Compounds

A. Properties

As detailed above, the antisense oligonucleotide analog compound (the term "antisense" indicates that the compound is targeted against either the virus' positive-sense strand RNA or negative-sense or minus-strand) has a base sequence targeting a region that includes one or more of the following; 1) the 5' or 3' terminal 30 bases of the negative sense viral RNA; 2) the terminal 30 bases of the 3' terminus of the positive sense mRNA and/or; 3) 50 bases surrounding the AUG start codons of viral mRNA. In addition, the oligomer is able to effectively target infecting viruses, when administered to a host cell, e.g. in an infected mammalian subject. This requirement is met when the oligomer compound (a) has the ability to be actively taken up by mammalian cells, and (b) once taken up, form a duplex with the target RNA with a Tm greater than about 45° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G: C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

B. Active or Facilitated Uptake by Cells

The antisense compound may be taken up by host cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3→P5' phosphoramidate linkages, and a comparable number of cationic linkages, such as N,N-diethylenediamine phosphoramidates (Dagle, Littig et al. 2000). The net charge is preferably neutral or at most 1-2 net charges per oligomer.

In addition to being substantially or fully uncharged, the antisense agent is preferably a substrate for a membrane transporter system (i.e. a membrane protein or proteins)

capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Felgner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked covalently to the 5' or 3' end of the antisense oligomer. The peptide is typically 8-16 amino acids and consists of a mixture of arginine, and other amino acids including phenyalanine and cysteine. The use of arginine-rich peptide-PMO conjugates can be used to enhance cellular uptake of the antisense oligomer (See, e.g. (Moulton, Nelson et al. 2004; Nelson, Stein et al. 2005). Exemplary arginine-rich peptides for use in practicing the invention are listed as SEQ ID NOs:25-30. Non-natural amino acids can be used in combination with naturally occuring amino acids as shown in the Sequence listing table for SEQ ID NOs:26-30. In these examples 6-aminohexanoic acid (Ahx) and/or beta-alanine (β-Ala) are used.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979).

Hydrogels may also be used as vehicles for antisense oligomer administration, for example, as described in WO 93/01286. Alternatively, the oligonucleotides may be administered in microspheres or microparticles. (See, e.g. Wu and Wu 1987). Alternatively, the use of gas-filled microbubbles complexed with the antisense oligomers can enhance delivery to target tissues, as described in U.S. Pat. No. 6,245,747.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

C. Substantial Resistance to RNaseH

Two general mechanisms have been proposed to account for inhibition of expression by antisense oligonucleotides. (See e.g., Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing or translation. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3→P5' phosphoramidates (Ding, Grayaznov et al. 1996; Gee, Robbins et al. 1998).

A test oligomer can be assayed for its RNaseH resistance by forming an RNA: oligomer duplex with the test compound, then incubating the duplex with RNaseH under a standard assay conditions, as described in Stein et al. After exposure to RNaseH, the presence or absence of intact duplex can be monitored by gel electrophoresis or mass spectrometry.

D. In Vivo Uptake

In accordance with another aspect of the invention, there is provided a simple, rapid test for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including a host RNA or the RNA of an infecting virus. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

When the antisense oligomer is complementary to a virus-specific region of the viral genome (such as those regions of influenza RNA, as described above) the method can be used to detect the presence of a given influenza virus, or reduction in the amount of virus during a treatment method.

E. Exemplary Oligomer Backbones

Figure 2A:
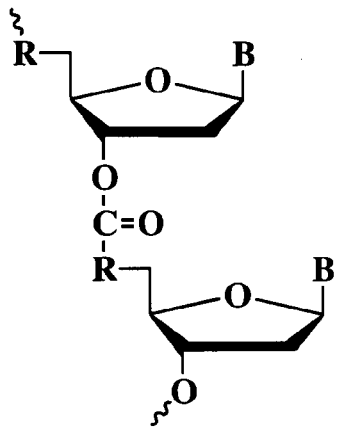
FIGS. 2A-2G show examples of uncharged linkage types in oligonucleotide analogs.
Figure 2B:
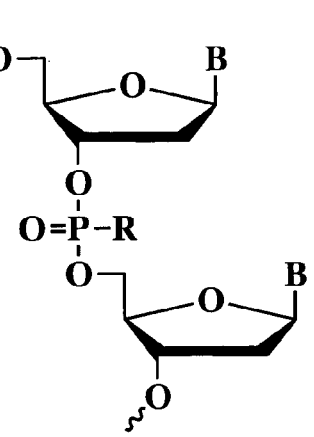
Figure 2C:
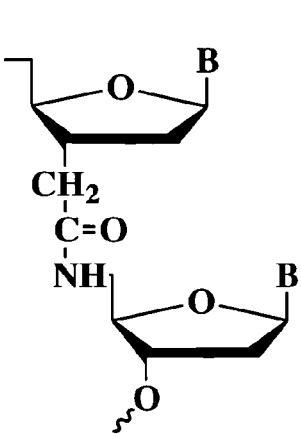
Figure 2D:
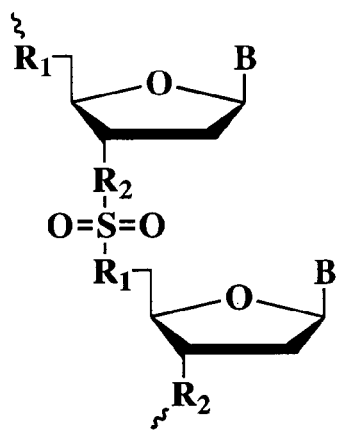
Figure 2E:
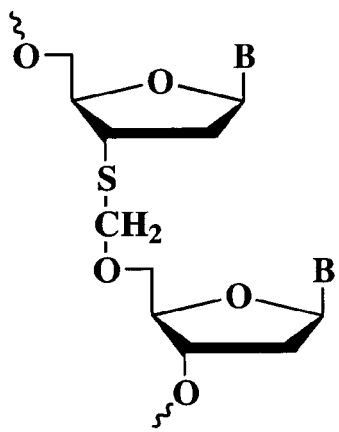
Figure 2F:
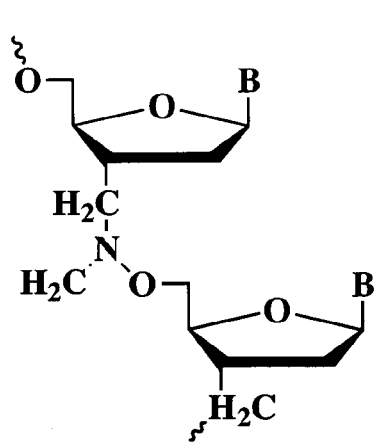
Figure 2G:
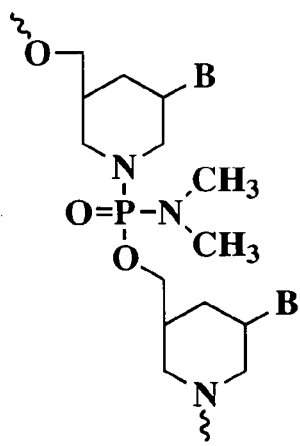
Figure 2H:
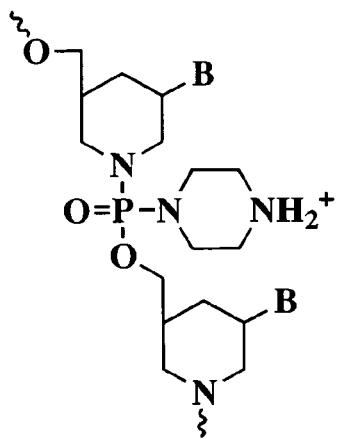
FIG. 2H shows an example of a cationic linkage group.

Examples of nonionic linkages that may be used in oligonucleotide analogs are shown in FIGS. 2A-2G. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (3A, R=O) and carbamate (2A, R=NH$_2$) linkages (Mertes and Coats 1969; Gait, Jones et al. 1974); alkyl phosphonate and phosphotriester linkages (2B, R=alkyl or —O-alkyl) (Lesnikowski, Jaworska et al. 1990); amide linkages (2C) (Blommers, Pieles et al. 1994); sulfone and sulfonamide linkages (2D, R$_1$, R$_2$=CH$_2$); and a thioformacetyl linkage (2E) (Cross, Rice et al. 1997). The latter is reported to have enhanced duplex and triplex stability with respect to phosphorothioate antisense compounds (Cross, Rice et al. 1997). Also reported are the 3'-methylene-N-methylhydroxyamino compounds of structure 2F. FIG. 2H is an example of a cationic linkage group.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D, and FIG. 2G. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types shown in FIGS. 1A-1D, each linked by an uncharged, phosphorus-containing subunit linkage. FIG. 1A shows a phosphorus-containing linkage which forms the five atom repeating-unit backbone, where the morpholino rings are linked by a 1-atom phosphoamide linkage. FIG. 1B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1C:
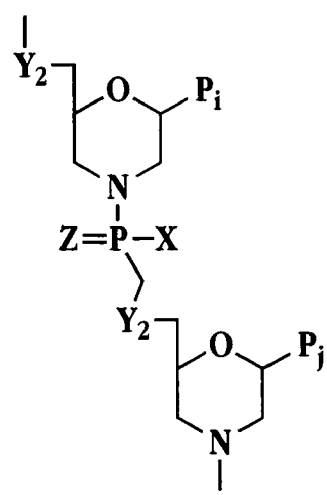
Figure 1D:
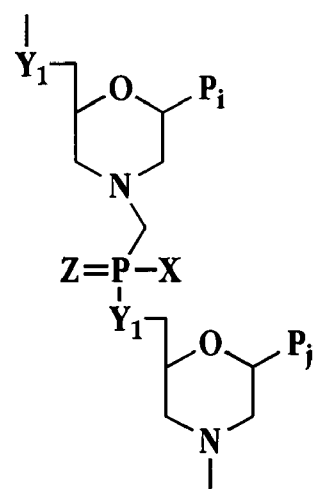

The linkages shown in FIGS. 1C and 1D are designed for 7-atom unit-length backbones. In Structure 1C, the X moiety is as in Structure 1B, and the Y moiety may be methylene, sulfur, or, preferably, oxygen. In Structure 1D, the X and Y moieties are as in Structure 1B. Particularly preferred morpholino oligonucleotides include those composed of morpholino subunit structures of the form shown in FIG. 1B, where X=NH$_2$ or N(CH$_3$)$_2$, Y=O, and Z=O.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

IV. Inhibition of Influenza Viral Replication

The antisense compounds detailed above are useful in inhibiting replication of single-stranded, negative-sense, segmented RNA viruses of the Orthomyxoviridae family. In one embodiment, such inhibition is effective in treating infection of a host animal by these viruses. Accordingly, the method comprises, in one embodiment, contacting a cell infected with the virus with a antisense agent effective to inhibit the replication of the specific virus. In this embodiment, the antisense agent is administered to a mammalian subject, e.g., human or domestic animal, infected with a given virus, in a suitable pharmaceutical carrier. It is contemplated that the antisense oligonucleotide arrests the growth of the RNA virus in the host. The RNA virus may be decreased in number or eliminated with little or no detrimental effect on the normal growth or development of the host.

In the present invention as described in the Examples, Phosphorodiamidate Morpholino Oligomers (PMOs), designed to hybridize to various gene segments of influenza A virus, were evaluated for their ability to inhibit influenza virus production in Vero cell culture. The PMOs were conjugated to a short arginine-rich peptide to facilitate entry into cells in culture. Vero cells were incubated with PMO compounds, inoculated with influenza virus, and viral titer determined by hemagglutinin assay and/or plaque-assay. The compounds targeting the AUG translation start-sites of polymerase component PB1 and nuclear capsid protein (NP), the 5' and 3' ends of vRNA NP segment and the 3'end of cRNA NP segment were very effective, reducing the titer of influenza virus by 1 to 3 orders of magnitude compared to controls, in a dose-dependent and sequence-specific manner over a period of 2 days. Combinations of some of the PMOs exhibited a synergistic antiviral effect as described in Example 3. These data indicate that several of the PMOs tested in this study are potential influenza A therapeutics.

The effective anti-influenza A PMO compounds were observed not to alter the titer of influenza B virus grown in Vero cells due to the lack of homology between the influenza A virus-specific PMOs and the corresponding influenza B virus targets. However, the PMO described herein (SEQ ID NOs:10-24) will target most, if not all, influenza A virus strains because of the high degree of homology between strains at the respective targets (SEQ ID NOs:1-9). An example of the sequence conservation at two preferred targets is shown in FIG. 4. In this case the sequence conservation between multiple isolates of H5N1 (e.g. bird flu) and H1N1 was determined for the targets of the PB1-AUG and (−) NP-3'trm PMOs (SEQ ID NOs:12 and 13, respectively). FIG. 4 shows a very high level of conservation at these target sites.

A. Identification of the Infective Agent

The specific virus causing the infection can be determined by methods known in the art, e.g. serological or cultural methods, or by methods employing the antisense oligomers of the present invention.

Serological identification employs a viral sample or culture isolated from a biological specimen, e.g., stool, urine, cerebrospinal fluid, blood, etc., of the subject. Immunoassay for the detection of virus is generally carried out by methods routinely employed by those of skill in the art, e.g., ELISA or Western blot. In addition, monoclonal antibodies specific to particular viral strains or species are often commercially available.

Culture methods may be used to isolate and identify particular types of virus, by employing techniques including, but not limited to, comparing characteristics such as rates of growth and morphology under various culture conditions.

Another method for identifying the viral infective agent in an infected subject employs one or more antisense oligomers targeting broad families and/or genera of viruses. Sequences targeting any characteristic viral RNA can be used. The desired target sequences are preferably (i) common to broad virus families/genera, and (ii) not found in humans. Characteristic nucleic acid sequences for a large number of infectious viruses are available in public databases, and may serve as the basis for the design of specific oligomers.

For each plurality of oligomers, the following steps are carried out: (a) the oligomer(s) are administered to the subject; (b) at a selected time after said administering, a body fluid sample is obtained from the subject; and (c) the sample is assayed for the presence of a nuclease-resistant heteroduplex comprising the antisense oligomer and a complementary portion of the viral genome. Steps (a)-(c) are carried for at least one such oligomer, or as many as is necessary to identify the virus or family of viruses. Oligomers can be administered and assayed sequentially or, more conveniently, concurrently. The virus is identified based on the presence (or absence) of a heteroduplex comprising the antisense oligomer and a complementary portion of the viral genome of the given known virus or family of viruses.

Preferably, a first group of oligomers, targeting broad families, is utilized first, followed by selected oligomers complementary to specific genera and/or species and/or strains within the broad family/genus thereby identified. This second group of oligomers includes targeting sequences directed to specific genera and/or species and/or strains within a broad family/genus. Several different second oligomer collections, i.e. one for each broad virus family/genus tested in the first stage, are generally provided. Sequences are selected which are (i) specific for the individual genus/species/strains being tested and (ii) not found in humans.

B. Administration of the Antisense Oligomer

Effective delivery of the antisense oligomer to the target nucleic acid is an important aspect of treatment. In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. For example, an appropriate route for delivery of an antisense oligomer in the treatment of a viral infection of the skin is topical delivery, while delivery of a antisense oligomer for the treatment of a viral respiratory infection is by inhalation. The oligomer may also be delivered directly to the site of viral infection, or to the bloodstream.

The antisense oligomer may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic viral infection. The condition of a patient may also dictate prophylactic administration of an antisense oligomer of the invention, e.g. in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In another application of the method, the subject is a livestock animal, e.g., a chicken, turkey, pig, cow or goat, etc, and the treatment is either prophylactic or therapeutic. The invention also includes a livestock and poultry food composition containing a food grain supplemented with a subtherapeutic amount of an antiviral antisense compound of the type described above. Also contemplated is, in a method of feeding livestock and poultry with a food grain supplemented with subtherapeutic levels of an antiviral, an improvement in which the food grain is supplemented with a subtherapeutic amount of an antiviral oligonucleotide composition as described above.

The antisense compound is generally administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 0.5 mg to 100 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

C. Monitoring of Treatment

An effective in vivo treatment regimen using the antisense oligonucleotides of the invention may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of viral infection under treatment, and corresponding adjustments in the dose or treatment regimen, in order to achieve an optimal therapeutic outcome. Treatment may be monitored, e.g., by general indicators of infection, such as complete blood count (CBC), nucleic acid detection methods, immunodiagnostic tests, viral culture, or detection of heteroduplex.

The efficacy of an in vivo administered antisense oligomer of the invention in inhibiting or eliminating the growth of one or more types of RNA virus may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of viral protein production, as determined by standard techniques such as ELISA or Western blotting, or (3) measuring the effect on viral titer, e.g. by the method of Spearman-Karber. (See, for example, Pari, G. S. et al., Antimicrob. Agents and Chemotherapy 39(5): 1157-1161, 1995; Anderson, K. P. et al., Antimicrob. Agents and Chemotherapy 40(9):2004-2011, 1996, Cottral, G. E. (ed) in: Manual of Standard Methods for Veterinary Microbiology, pp. 60-93, 1978).

A preferred method of monitoring the efficacy of the antisense oligomer treatment is by detection of the antisense-RNA heteroduplex. At selected time(s) after antisense oligomer administration, a body fluid is collected for detecting the presence and/or measuring the level of heteroduplex species in the sample. Typically, the body fluid sample is collected 3-24 hours after administration, preferably about 6-24 hours after administering. As indicated above, the body fluid sample may be urine, saliva, plasma, blood, spinal fluid, or other liquid sample of biological origin, and may include cells or cell fragments suspended therein, or the liquid medium and its solutes. The amount of sample collected is typically in the 0.1 to 10 ml range, preferably about 1 ml or less.

The sample may be treated to remove unwanted components and/or to treat the heteroduplex species in the sample to remove unwanted ssRNA overhang regions, e.g., by treatment with RNase. It is, of course, particularly important to remove overhang where heteroduplex detection relies on size separation, e.g., electrophoresis of mass spectroscopy.

A variety of methods are available for removing unwanted components from the sample. For example, since the heteroduplex has a net negative charge, electrophoretic or ion exchange techniques can be used to separate the heteroduplex from neutral or positively charged material. The sample may also be contacted with a solid support having a surface-bound antibody or other agent specifically able to bind the heteroduplex. After washing the support to remove unbound material, the heteroduplex can be released in substantially purified form for further analysis, e.g., by electrophoresis, mass spectroscopy or immunoassay.

V. Examples

The following examples illustrate but are not intended in any way to limit the invention.

A. Materials and Methods

Standard recombinant DNA techniques were employed in all constructions, as described in Ausubel, F M et al., in CURRENT PROTOCOLS IN MOLECULAR BIOLOGY, John Wiley and Sons, Inc., Media, Pa., 1992 and Sambrook, J. et al., in MOLECULAR CLONING: A LABORATORY MANUAL, Cold Spring Harbor Laboratory Press, Cold Spring Harbor, N.Y., Vol. 2, 1989).

All peptides were custom synthesized by Global Peptide Services (Ft. Collins, Colo.) or at AVI BioPharma (Corvallis, Oreg.) and purified to >90% purity (see Example 2 below). PMOs were synthesized at AVI BioPharma in accordance with known methods, as described, for example, in ((Summerton and Weller 1997) and U.S. Pat. No. 5,185,444. The structure of the PMO is as shown in FIG. 2G.

PMO oligomers were conjugated at the 5' end with an arginine-rich peptide ($R_5F_2R_4C$-5'-PMO, SEQ ID NO:25) to enhance cellular uptake as described (U.S. Patent Application 60/466,703 and (Moulton, Nelson et al. 2004; Nelson, Stein et al. 2005).

B. Example 1

Inhibition of Influenza A virus in Cell Culture with Phosphorodiamidate Morpholino Oligomers Phosphorodiamidate Morpholino Oligomers (PMOs), designed to hybridize to various gene segments of influenza A virus, were evaluated for their ability to inhibit influenza virus production in Vero cell culture. The PMOs were conjugated to a short arginine-rich peptide ($R_5F_2R_4C$) to facilitate entry into cells in culture. Vero cells were incubated with PMO compounds, inoculated with influenza A virus (strain PR8, H1N1), and viral titer determined by hemagglutinin assay (HA) and/or plaque-assay (CFU). The PMO compounds targeting the AUG translation start-sites of polymerase component PB1 and nuclear capsid protein (NP) (SEQ ID NOs:10 and 11), the 5' and 3' ends of the NP gene (SEQ ID NOs:13 and 14) encoded by the viral RNA (i.e. vRNA) and the 3' end of the NP gene (SEQ ID NO: 15) encoded by the complementary RNA (cRNA) were very effective in reducing the titer of influenza virus by 1 to 3 orders of magnitude compared to controls, in a dose-dependent and sequence-specific manner over a period of 2 days.

Figure 5A:
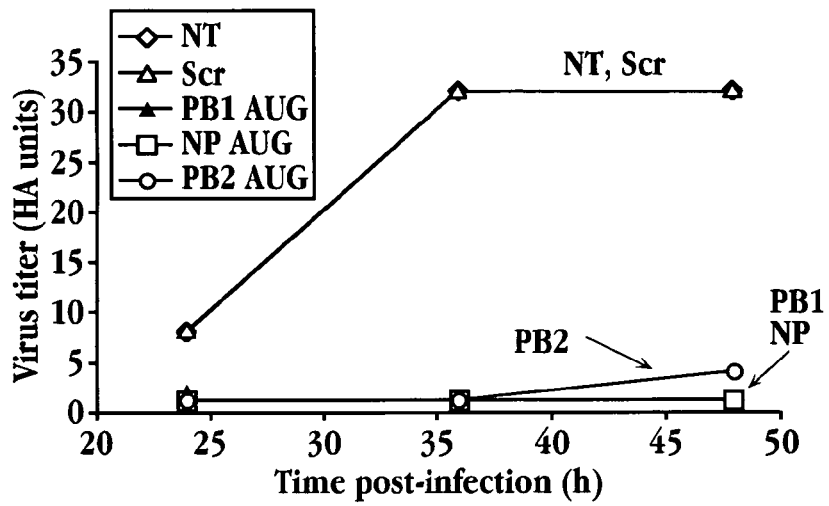
FIGS. 5A-5B show the effect of 20 mM AUG-targeted and termini-targeted PMO on influenza virus replication in infected Vero cells.
Figure 5B:
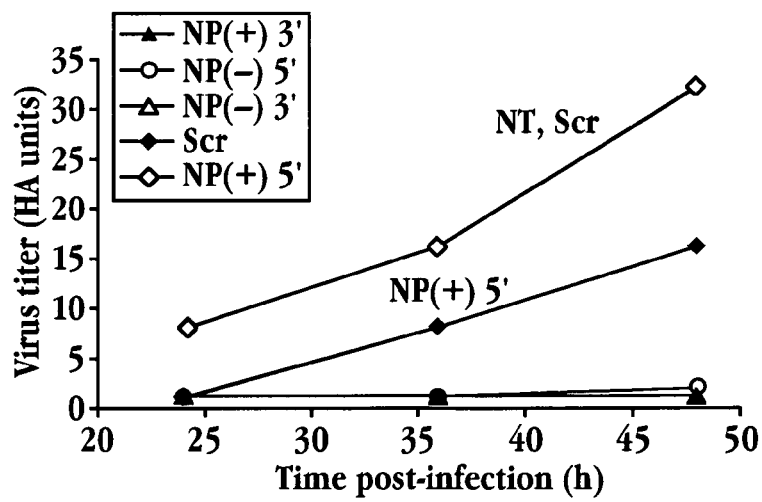
Figure 5C:
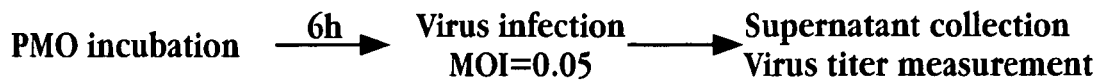
FIG. 5C describes the experimental protocol.

FIG. 5 shows the effect of 20 µM AUG-targeted and 5' and 3' termini-targeted PMOs on influenza A virus production in Vero cells compared to untreated (NT) and a scramble control PMO (Scr). Vero cells were preincubated with PMO for 6 hours followed by virus infection at a multiplicity of infection (M.O.I.) of 0.05. At various times post-infection, supernatant was collected for determination of virus titer as measured by a Hemaglutinin Assay (HA). Three PMO targeting AUG start codons of the NP, PB1 and PB2 genes were effective at reducing influenza virus replication (SEQ ID NOs:10-12) as shown in FIG. 5. Two PMOs that target the 5' and 3'-termini of vRNA, NP(−)5' and NP(−)3' (SEQ ID NOs:13 and 14) and one PMO that targets the 3' termini of the cRNA, NP(+)3' (SEQ ID NO:15) were effective at reducing influenza virus replication in this assay as shown in FIG. 5. The PMO that targets the 5' termini of the cRNA, NP(+)5' (SEQ ID NO:24), was less effective but still demonstrated anti-viral activity.

Figure 6A:
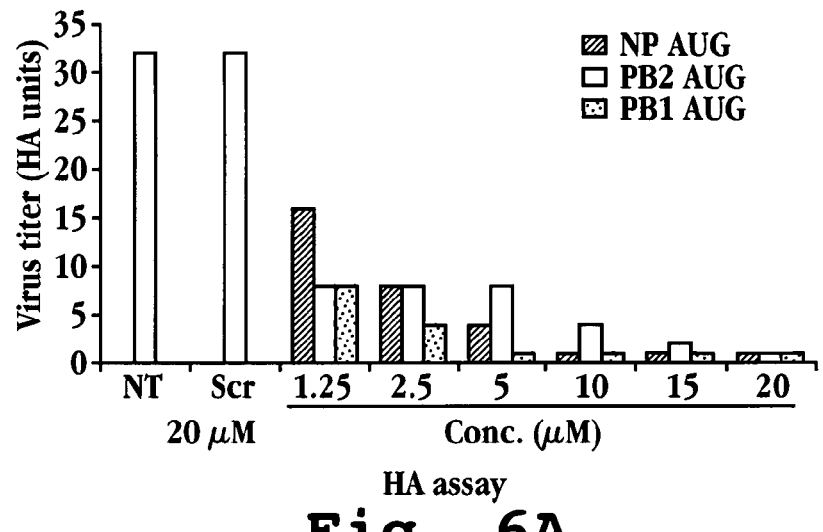
FIG. 6 shows the dose response of AUG-targeted PMO on influenza virus replication in Vero cells using the hemagglutinin assay (6A) and the plaque assay techniques (6B).
FIG. 6C describes the experimental protocol.
Figure 6B:
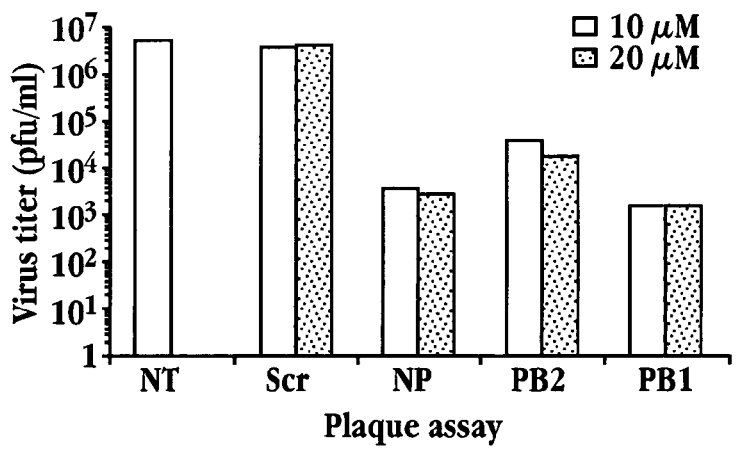
Figure 6C:
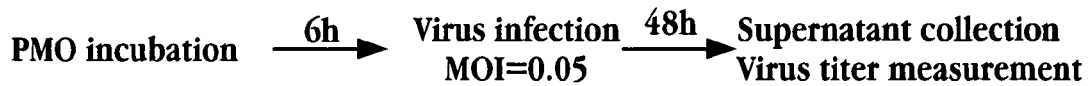
Figure 7A:
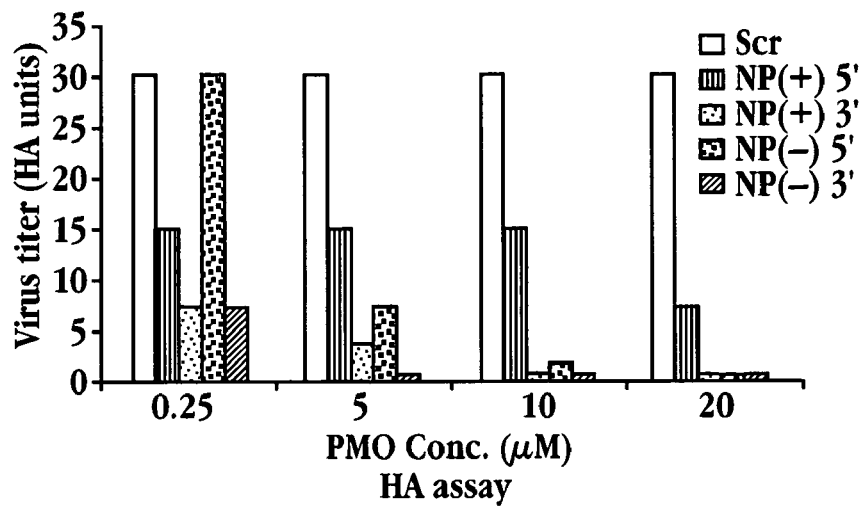
FIGS. 7A-7B show the dose response of termini-targeted PMO on influenza virus replication in Vero cells using the same assays as in FIG. 6.
Figure 7B:
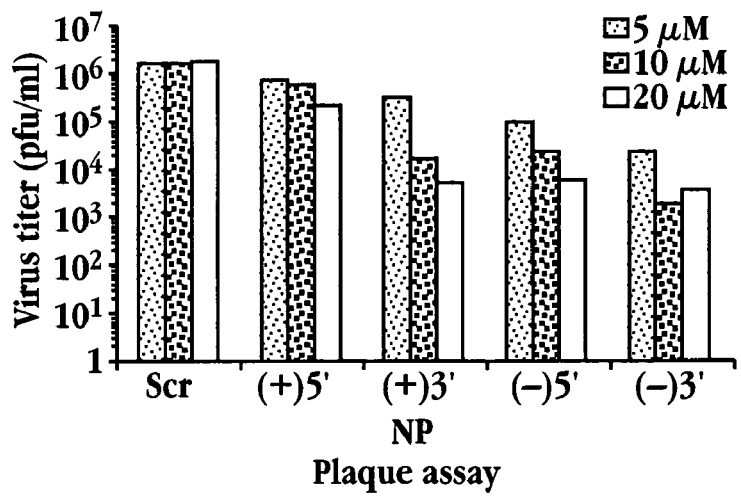
Figure 7C:
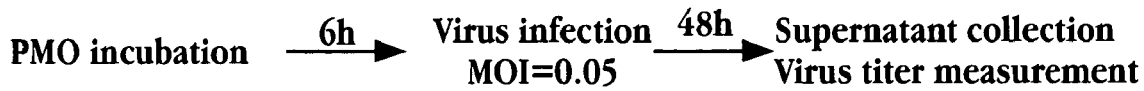
FIG. 7C describes the experimental protocol.

PMOs that target the AUG start codons of three influenza virus genes, NP-AUG, PB2-AUG and PB1-AUG (SEQ ID NOs: 0-12, respectively) were assayed for their ability to inhibit influenza A virus replication in a dose response assay using the hemagglutinin assay and the plaque-forming assay. The results are shown in FIG. 6. For all three PMOs the concentration that effectively resulted in a 50% reduction in viral replication (EC50) was found to be less than 1 µM. A three-log reduction in viral replication using the plaque assay was observed for two of the PMOs, NP-AUG and PB1-AUG at 10 µM. Identical assays were performed using the termini-targeted PMO: NP(−)3', NP(−)5', NP(+)3' and NP(+)5' (SEQ ID NOs:13, 14, 15 and 24, respectively). All four PMOs demonstrated significant reduction in viral titer as shown in FIG. 7.

C. Example 2

Effect of PMO Targeting the 3'-Terminus of NP vRNA on NP mRNA and cRNA Transcription Quantitative RTPCR was used to determine the effect of one of the termini-targeted PMO, NP(−)3' (SEQ ID NO:13) on the transcription of the NP vRNA segment into mRNA and cRNA species (i.e., see FIG. 4). The mRNA transcription product is positive-sense RNA whereas the cRNA is a negative-sense RNA. The NP(−)3' PMO was incubated with Vero cells for 6 hours followed by influenza A virus infection at an MOI of 0.05. Three hours post-infection, RNA was isolated and RNA species specific reverse transcription (RT) was performed followed by quantitative PCR on the reaction product. FIG. 8 shows that the NP(−)3' PMO (SEQ ID NO:13) that targets the 3' end of the vRNA strongly suppressed the transcription of NP mRNA and cRNA.

D. Example 3

Figure 9A:
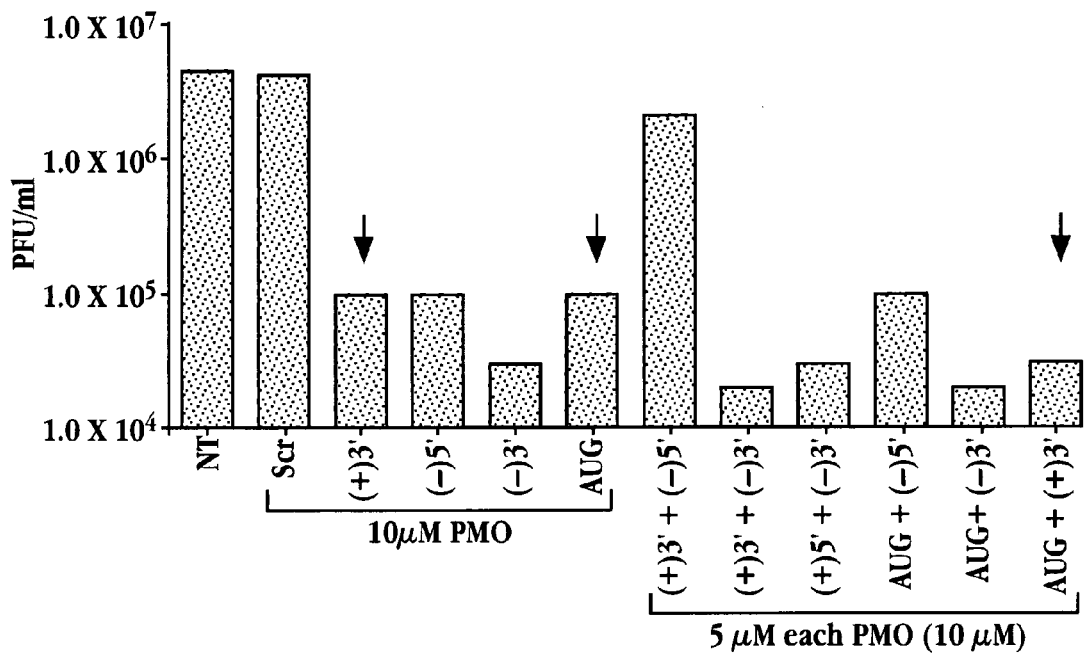
FIG. 9A shows the synergistic effect of PMO that target the termini of the NP segment and the NP gene AUG start codon on influenza A virus replication in Vero cells.
Figure 9B:
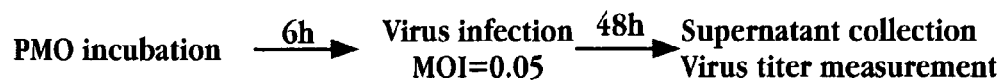
FIG. 9B describes the experimental protocol.

Synergistic Inhibition of Influenza A Virus Replication in Cell Culture Using Combinations of Anti-Influenza PMO Combinations of some of the PMOs exhibited a synergistic antiviral effect. FIG. 9 shows the synergistic effect of various combinations of PMO that target the NP vRNA termini and the NP-AUG region. PMO treatment and influenza A virus infection were as described in Example 1. The plaque assay was used to measure virus replication. Three termini-targeted PMO, NP(−)3', NP(−)5', NP(+)3' (SEQ ID NOs:13-15) and the NP-AUG PMO (SEQ ID NO:10) were mixed in various combinations as shown in FIG. 8. One combination, NP(+)3' with NP(−)5' did not produce antiviral activity as this pair of PMO are predicted to hybridize to each other. All the other PMO combinations demonstrated significant inhibition of influenza A viral replication.

Sequence Listing

| | SEQ ID NO |
|---|---|
| Target Sequences (5' to 3') | |
| UCACUCACUGAGUGACAUCAAAAUCAUGGCGUCCCAAGGCACCAAACGGU | 1 |
| AGCGAAAGCAGGUCAAUUAUAUUCAAUAUGGAAAGAAUAAAAGAACUAAG | 2 |
| AGCCAAAGCAGGCAAACCAUUUGAAUGGAUGUCAAUCCGACCUUACUUUU | 3 |
| AAAGAAAAAUACCCUUGUUUCUACU | 4 |
| AGCAAAAGCAGGGUAGAUAAUCACU | 5 |
| CAUGAAAAAAUGCCUUGUUCCUACU | 6 |
| AGCGAAAGCAGGCAAACCAUUUCAA | 7 |
| CUUUAAAAACGACCUUGUUUCUACU | 8 |
| AGCGAAAGCAGGUCAAUUAUAUUCA | 9 |
| Oligomer Targeting Sequences (5' to 3') | |
| CTTGGGACGCCATGATTTTG | 10 |
| CTTTTATTCTTTCCATATTG | 11 |
| GACATCCATTCAAATGGTTTG | 12 |
| AGCAAAAGCAGGGTAGATAATC | 13 |
| GAAAAATACCCTTGTTTCTACT | 14 |
| AGTAGAAACAAGGGTATTTTTC | 15 |

|                                   | SEQ ID NO |
|---|---|
| ACCAAAAGCAGG                      | 16 |
| AGTAGAAACAAGG                     | 17 |
| AGCGAAAGCAGGCAAACCAT              | 18 |
| GAAAAATGCCTTGTTCCTACT             | 19 |
| AGTAGGAACAAGGCATTTTTTC            | 20 |
| AGCGAAAGCAGGTCAATTAT              | 21 |
| TAAAAACGACCTTGTTTCTACT            | 22 |
| AGTAGAAACAAGGTCGTTTTTA            | 23 |

|                                   | SEQ ID NO |
|---|---|
| AGTCTCGACTTGCTACCTCA              | 24 |
| Peptide Sequences                 |    |
| $R_5F_2R_4C$                      | 25 |
| $(RAhxR)_4Ahx\beta Ala$           | 26 |
| $(RAhx)_8\beta Ala$               | 27 |
| $(RAhx)_4\beta Ala$               | 28 |
| $(RAhxR)_2Ahx\beta Ala$           | 29 |
| $(RAhxR)_3Ahx\beta Ala$           | 30 |

It is claimed:

1. A method of treating influenza virus A infection in a mammalian subject, comprising:
   administering by inhalation to the mammalian subject, a therapeutically effective amount of an antisense conjugate comprising
   a substantially uncharged antisense oligonucleotide composed of morpholino subunits linked by phosphorus-containing intersubunit linkages which join a morpholino nitrogen of one subunit to a 5' exocyclic carbon of an adjacent subunit, and having a targeting sequence of at least 12 contiguous bases that are complementary to SEQ ID NO: 3, and
   an arginine-rich carrier peptide having the sequence identified by SEQ ID NO: 26 covalently attached to the oligonucleotide,
   wherein said therapeutically effective amount is an amount effective to reduce viral titer in said subject by at least tenfold compared to an untreated or nonsense-treated control.

2. The method of claim 1, wherein the oligonucleotide analog is 12-40 nucleotide bases in length and targets an AUG start codon of the PB1 viral mRNA.

3. The method of claim 1, wherein the conjugate forms with a complementary-sequence viral target region contained in SEQ ID NO: 3, a heteroduplex having a Tm of dissociation of at least 45° C.

4. The method of claim 1, wherein the intersubunit linkages are uncharged.

5. The method of claim 1, wherein the morpholino subunits are joined by intersubunit linkages in accordance with the structure:

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or —$NR_2$, and wherein each R is independently hydrogen or lower alkyl.

6. The method of claim 5, wherein X is —$NR_2$ and each R is a lower alkyl.

7. The method of claim 1, wherein the oligonucleotide in the conjugate has the sequence identified by SEQ ID NO:12.

* * * * *